US011633249B2

(12) United States Patent
Smaby et al.

(10) Patent No.: US 11,633,249 B2
(45) Date of Patent: Apr. 25, 2023

(54) ASSEMBLY PROCESS FOR TENSIONING ELEMENTS AND RELATED SYSTEMS

(71) Applicant: Intuitive Surgical Operations, Inc., Sunnyvale, CA (US)

(72) Inventors: Niels Smaby, Palo Alto, CA (US); Amir Chaghajerdi, San Jose, CA (US); James Trevor Clark, Mountain View, CA (US); Stephen V. Gentile, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1493 days.

(21) Appl. No.: 15/880,331

(22) Filed: Jan. 25, 2018

(65) Prior Publication Data

US 2018/0228563 A1 Aug. 16, 2018

Related U.S. Application Data

(60) Provisional application No. 62/457,683, filed on Feb. 10, 2017.

(51) Int. Cl.
*B25J 9/10* (2006.01)
*A61B 34/00* (2016.01)
*A61B 34/35* (2016.01)

(52) U.S. Cl.
CPC ............. *A61B 34/71* (2016.02); *A61B 34/35* (2016.02); *B25J 9/1045* (2013.01); *A61B 34/76* (2016.02); *A61B 2034/715* (2016.02)

(58) Field of Classification Search
None
See application file for complete search history.

(56) References Cited

U.S. PATENT DOCUMENTS

2012/0150192 A1* 6/2012 Dachs, II ............... A61B 34/30
606/130
2016/0166340 A1* 6/2016 Brudniok ............... A61B 34/30
606/130

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

Primary Examiner — Chinyere J Rushing-Tucker
(74) Attorney, Agent, or Firm — Fish & Richardson P.C.

(57) ABSTRACT

A method of manufacturing a surgical instrument mountable to a remotely controllable manipulator configured to operate the surgical instrument includes applying a first tension to a first tensioning element, applying a second tension to a second tensioning element, and maintaining the first and second tensions in the first and second tensioning elements while a first rotatable cylinder is locked to a second rotatable cylinder. The first tensioning element and the second tensioning element are each coupled to a distal end component of the surgical instrument and are coupled to one another such that a tension in one of the first tensioning element and the second tensioning element is transmitted at least in part to the other of the first tensioning element and the second tensioning element.

22 Claims, 15 Drawing Sheets

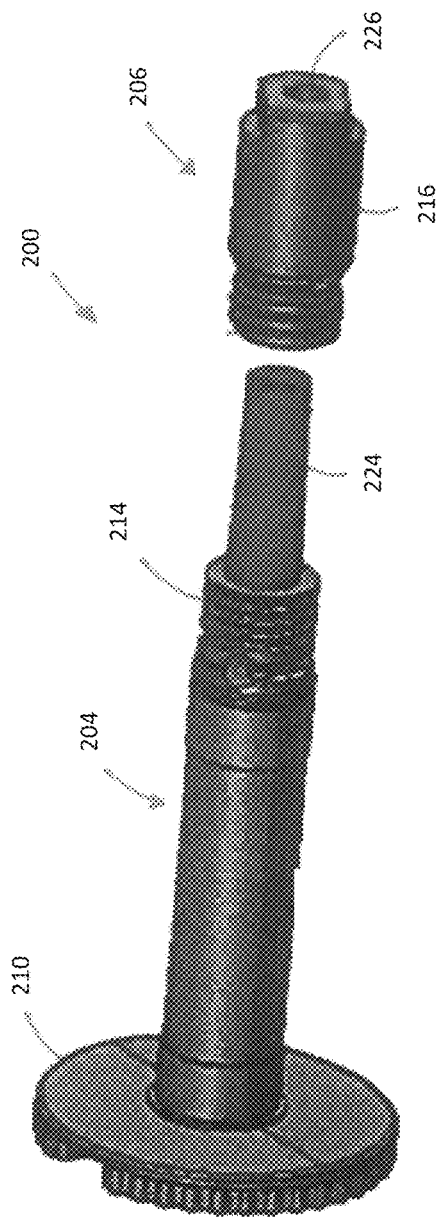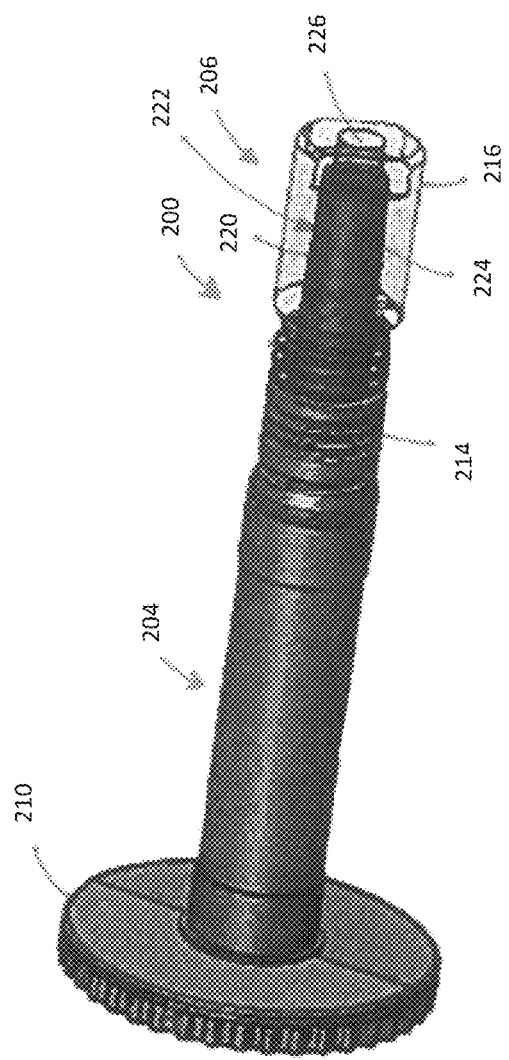
FIG. 8A
FIG. 8B

ASSEMBLY PROCESS FOR TENSIONING ELEMENTS AND RELATED SYSTEMS

TECHNICAL FIELD

This specification relates to processes to apply preloads to tensioning elements and related systems.

BACKGROUND

Minimally invasive medical techniques (e.g., laparoscopy) can be used to reduce the amount of extraneous tissue that may be damaged during diagnostic or surgical procedures, thereby reducing patient recovery time, discomfort, and deleterious side effects. Such techniques can be by a surgeon manually manipulating various surgical instruments within the patient's body. These techniques can also be implemented using teleoperated robotic systems that provide telepresence. Performing minimally invasive surgery with teleoperated robotic systems can facilitate increased precision and range of motion in manipulating surgical instruments when compared to manual techniques. In some examples, a surgical instrument can include tensioning elements that are driven in response to actuation by the surgeon or actuation by the teleoperated robotic system. Applying tension to the tensioning elements can drive, e.g., cause motion of, a distal end component of the surgical instrument. Preloads, e.g., loads on the tensioning elements absent driving operations on the surgical instrument during a surgical procedure, can be applied to the tensioning elements to enable the distal end component to respond more rapidly. In addition, preloads can be applied to improve controllability of the distal end component when the distal end component is directed toward a target pose.

SUMMARY

In one aspect, a method of manufacturing a surgical instrument mountable to a remotely controllable manipulator configured to operate the surgical instrument includes applying a first tension to a first tensioning element coupled to a first rotatable cylinder of the surgical instrument by using a first motor to apply a first torque to the first rotatable cylinder. The method further includes applying a second tension to a second tensioning element coupled to a second rotatable cylinder of the surgical instrument by using a second motor to apply a second torque to the second rotatable cylinder. The method also includes maintaining the first and second tensions in the first and second tensioning elements while the first rotatable cylinder is locked to the second rotatable cylinder. The first tensioning element and the second tensioning element are each coupled to a distal end component of the surgical instrument and are coupled to one another such that a tension in one of the first tensioning element and the second tensioning element is transmitted at least in part to the other of the first tensioning element and the second tensioning element.

In a further aspect, a system includes a surgical instrument mountable to a remotely controllable manipulator. The surgical instrument includes a distal end component, a first and second rotatable cylinders, and a first and second tensioning element each coupled to the distal end component. The first tensioning element is coupled to the first rotatable cylinder, and the second tensioning element is coupled to the second rotatable cylinder. The first tensioning element and the second tensioning element are coupled to one another such that a tension in one of the first tensioning element and the second tensioning element is transmitted at least in part to the other of the first tensioning element and the second tensioning element. The system further includes a first motor to be coupled to the first rotatable cylinder, a second motor to be coupled to the second rotatable cylinder, and a controller. The first motor is configured to apply a first tension to a first tensioning element when the first motor is coupled to the first rotatable cylinder. The second motor is configured to apply a second tension to the second tensioning element when the second motor is coupled to the second rotatable cylinder. The controller is operable with the first and second motors to maintain the first tension in the first tensioning element and the second tension in the second tensioning element while the first rotatable cylinder is locked to the second rotatable cylinder.

In yet another aspect, a method of manufacturing a surgical instrument mountable to a remotely controllable manipulator configured to operate the surgical instrument includes applying a tension to a first tensioning element coupled to a first rotatable cylinder of the surgical instrument by using a first motor to rotate the first rotatable cylinder relative to a second rotatable cylinder of the surgical instrument. The method further includes maintaining the tension in the first tensioning element and maintaining the tension in a second tensioning element coupled to the second rotatable cylinder while the first rotatable cylinder is locked to the second rotatable cylinder. The first tensioning element and the second tensioning element are coupled to a distal end component of the surgical instrument and are configured such that a tension in one of the first tensioning element and the second tensioning element is transmitted at least in part to the other of the first tensioning element and the second tensioning element.

Implementations can include one or more of the features described below and herein elsewhere.

In some implementations, applying the first tension and the second tension includes applying the first tension and the second tension based on an operator input indicative of target tensions.

In some implementations, the method further includes removing constructional stretch from each of the first and second tensioning elements before applying the first and second tensions to the first and second tensioning elements. In some cases, the method further includes relaxing the first and second tensioning elements after removing the constructional stretch and before applying the first and second tensions to the first and second tensioning elements. In some cases, removing the constructional stretch from each of the first and second tensioning elements includes cyclically applying tension to each of the first and second tensioning elements.

In some implementations, the first rotatable cylinder is manually lockable to the second rotatable cylinder, and the method further includes providing operator feedback when an operator manually locks the first and second rotatable cylinders together. In some cases, the method further includes measuring positions of the first and second rotatable cylinders to monitor a loop length, and providing the operator feedback to maintain the loop length. In some cases, measuring the positions of the first and second rotatable cylinders includes measuring positions of the first and second motors based on signals from encoders coupled to the first and second motors.

In some implementations, the method further includes locking the first and second rotatable cylinders by translating the second rotatable cylinder toward the first rotatable cylinder.

In some implementations, applying the first tension to the first tensioning element includes applying the first tension to the first tensioning element based on a friction force on the first tensioning element. Applying the second tension to the second tensioning element includes, for example, applying the second tension to the second tensioning element based on a friction force on the second tensioning element.

In some implementations, the first tension and the second tension are applied while a position of an instrument joint coupled to the first and second tensioning elements is maintained.

In some implementations, the method further includes applying a third tension to the first tensioning element while the first and second rotatable cylinders are engaged such that a tension in the second tensioning element is substantially zero, applying a fourth tension to the second tensioning element while the first and second rotatable cylinders are engaged such that a tension in the first tensioning element is substantially zero, and then estimating a difference between an amount of rotation when the third tension is applied and an amount of rotation when the fourth tension is applied. The first tension and the second tension are applied to the first tensioning element and the second tensioning element, respectively, when the difference exceeded a predefined threshold In some implementations, the first tension and the second tension are applied while the first rotatable cylinder and the second rotatable cylinder are disengaged from one another, and the method further includes engaging the first rotatable cylinder to the second rotatable cylinder.

In some implementations, the first tensioning element and the second tensioning element are mechanically coupled such that a tension in one of the first tensioning element and the second tensioning element is transmitted at least in part to the other of the first tensioning element and the second tensioning element.

In some implementations, the surgical instrument includes an instrument joint movable to reposition the distal end component, and the first and second tensioning elements form a cable having a first end attached to the first rotatable cylinder and a second end attached to the second rotatable cylinder. The cable, for example, passes through the instrument joint such that a tension applied to the cable controls a position of the distal end component.

In some implementations, the surgical instrument includes an instrument joint movable to reposition the distal end component, the first tensioning element includes a first end attached to the first rotatable cylinder, and the second tensioning element includes a first end attached to the second rotatable cylinder. The first and second tensioning elements each include, for example, a second end attached to the instrument joint such that the first and second tensions applied to the first and second tensioning elements control a position of the distal end component.

In some implementations, the system further includes a mount configured to be coupled to the distal end component to maintain a position of the distal end component while the first and second motors apply the first and second tensions to the first and second tensioning elements, respectively.

In some implementations, the system further includes a first drive mechanism coupled to the first motor and configured to be coupled to the first rotatable cylinder, and a second drive mechanism coupled to the second motor and configured to be coupled to the second rotatable cylinder. The controller is configured, for example, to maintain the first tension in the first tensioning element and the second tension in the second tensioning element based on friction in the first drive mechanism and friction in the second drive mechanism.

In some implementations, the system further includes encoders coupled to the first and second motors. The controller is, for example, configured to provide operator feedback to maintain a loop length based on signals from the encoders while an operator manually locks the first rotatable cylinder the second rotatable cylinder.

In some implementations, the system further includes a third motor to be coupled to the second rotatable cylinder. The third motor is, for example, configured to couple the second motor with the second rotatable cylinder. In some cases, the third motor is configured to drive the second rotatable cylinder toward the first rotatable cylinder to rotationally couple the first rotatable cylinder to the second rotatable cylinder.

Advantages of the foregoing may include, but are not limited to, those described below and herein elsewhere. The preloads on the tensioning elements of the surgical instrument can be selected such that the distal end component of the surgical instrument can be more responsive to torque applied to the drivetrains driving the tensioning elements. These preloads can be more precisely established and, in particular, be tailored to ranges appropriate for the type of the surgical instrument.

In some examples, the operation of applying the preloads to the tensioning elements can be performed in an automated manner that can reduce the amount of time required to set the preloads on the tensioning elements. The automation of this operation can also reduce the likelihood of human operator errors.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

FIG. 8A is a perspective side view of another example of an input device with drive shafts in a disengaged state.

FIG. 8B is a perspective side view of the input device of FIG. 8A with the drive shafts in an engaged state.

Like reference numbers and designations in the various drawings indicate like elements.

DETAILED DESCRIPTION

Various implementations of the present disclosure relate to surgical instruments for use with teleoperated robotic systems. The surgical instruments may feature drive assemblies including tensioning elements that are more easily preloaded during manufacturing and assembly than in prior systems.

Minimally invasive surgery can be performed by inserting surgical instruments through orifices in a patient's body (e.g., natural orifices or body-wall incisions) and controlling the surgical instruments via an interface on the outside of the body. In various implementations of the present disclosure, the surgical instruments are teleoperated by surgeons. Thus, the surgeons do not move the instruments by direct physical contact, but instead control instrument motion from some distance away by moving master controllers. The operating surgeon is typically provided with a view of the actual surgical site via a visual display, so that the surgeon may remotely perform surgical motions on the master controllers while viewing the surgical site. A controller of the surgical system causes the surgical instrument to be moved in accordance with movement of the master controllers.

Example Surgical Systems

Figure 1:
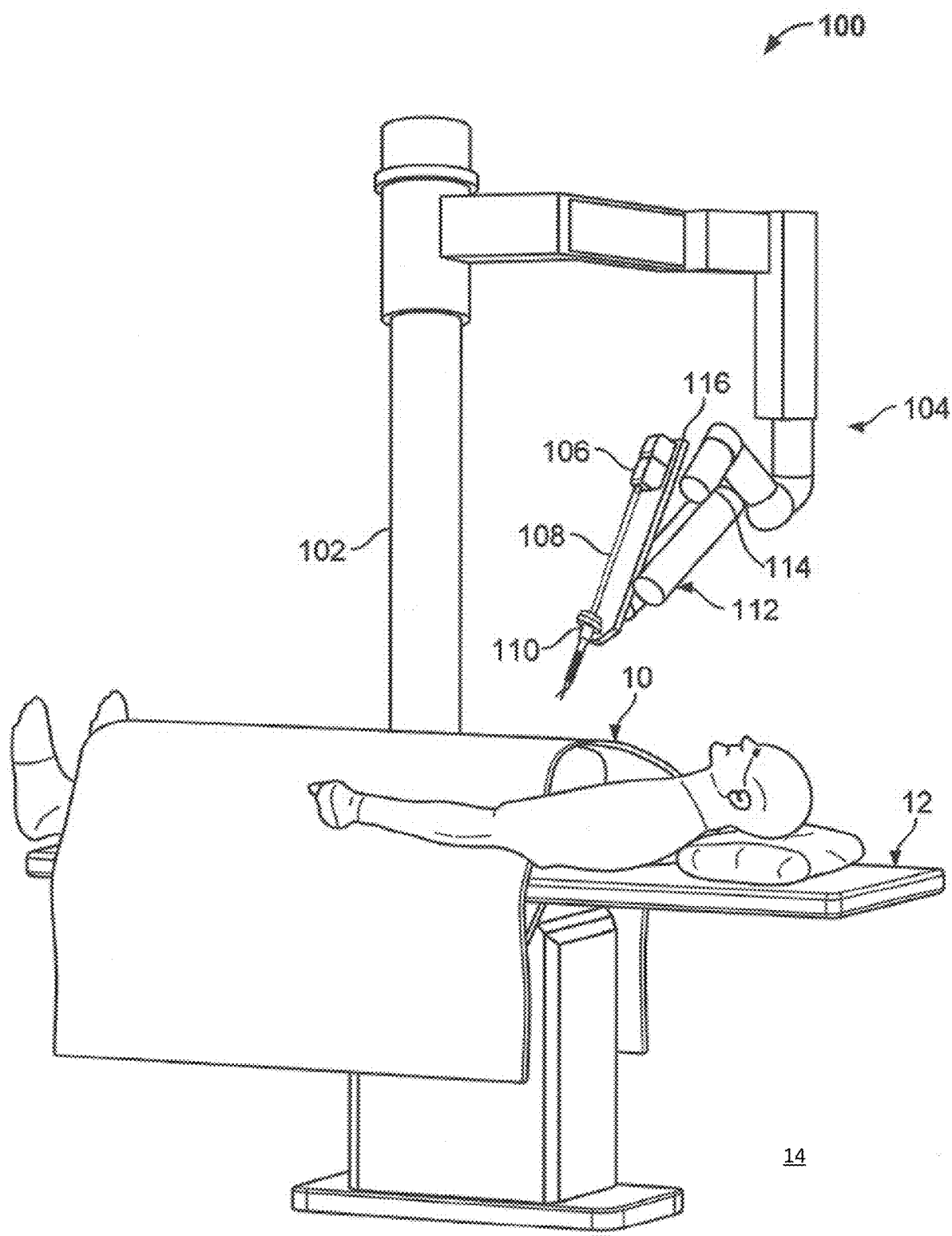
FIG. 1 is a perspective view of a portion of a teleoperated surgical system including a surgical instrument.
Figure 2:
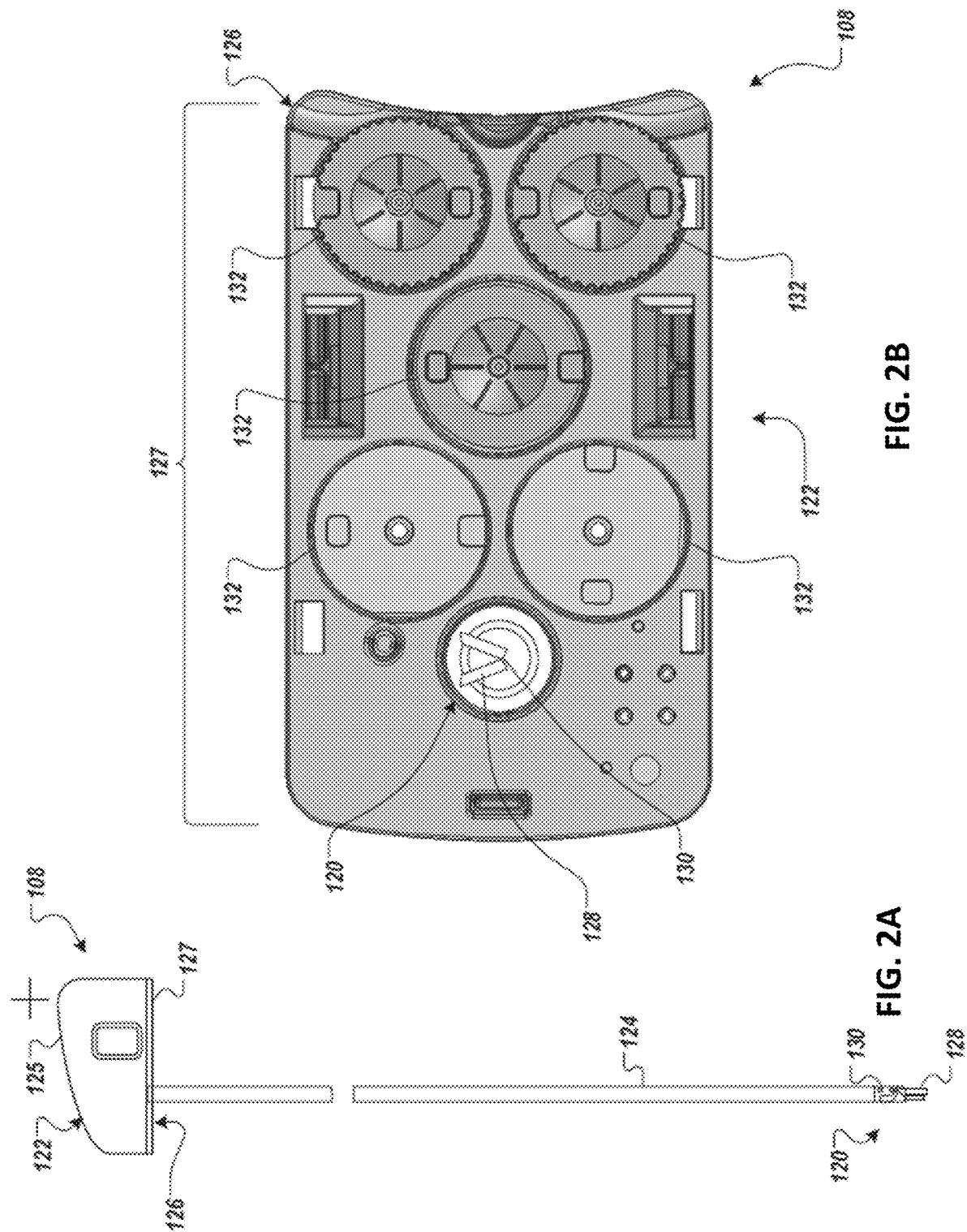
FIG. 2A is a side view of a surgical instrument including a drive assembly having an example of an input device.
FIG. 2B is a bottom view of the drive assembly of FIG. 2A.

FIG. 1 depicts a patient-side assembly 100 of a teleoperated surgical system in accordance with one or more implementations of the present invention. The patient-side assembly 100 is a robotic system for performing minimally invasive surgery on a body of a patient 10 positioned on an operating table 12. The patient-side assembly 100 includes a column 102, a support assembly 104, and an instrument carriage 106. The column 102 fixes the patient-side assembly 100 on a floor surface 14 proximate an operating table 12 supporting the patient 10. The support assembly 104 extends from the column 102, e.g., toward the patient 10 so that a remotely controllable manipulator 112 of the patient-side assembly 100 can more easily reach the patient 10. While the patient-side assembly 100 is described as being fixed to the floor surface, in some implementations, the patient-side assembly is mounted to a wall, to the ceiling, to the operating table supporting the patient's body, or to other operating room equipment.

The support assembly 104 extends radially outward from the column 102, and the instrument carriage 106 is positioned at a distal end of the support assembly 104. The instrument carriage 106 supports a detachable surgical instrument 108, and the instrument carriage 106 includes various actuators and control connections for controlling functionality of the instrument during a surgical procedure within the body of the patient 10. In particular, the actuators are teleoperated actuators housed in the instrument carriage 106. The actuators are, for example, remotely operated to selectively move an end effector of the surgical instrument 108. The surgical instrument 108 includes a drive assembly housing an input device configured to facilitate controlled adjustment of the end effector, in response to actuation signals from the instrument carriage. Examples of the drive assembly and the input device are described herein, e.g., with respect to FIGS. 2A-9B.

Returning to FIG. 1, an entry guide 110, e.g., a cannula, serves as a surgical port to an orifice of the body of the patient 10 that receives the surgical instrument 108 to guide the instrument into the patient 10. The entry guide 110 may perform various other functions, such as allowing fluids and other materials to pass into or out of the body, and reducing trauma at the surgical site by isolating at least some motion of the surgical instrument 108 relative to the body wall of the patient 10, e.g., translating movement along an insertion axis, and/or axial (lengthwise) rotation of the instrument shaft around the insertion axis.

The manipulator 112 is coupled to the support assembly 104. The manipulator 112 is operable to control positioning of the surgical instrument 108 relative to the body of the patient 10. In some implementations, the manipulator 112 is provided in a variety of forms that allow surgical instrument 108 to move with one or more mechanical degrees of freedom (DOFs). The manipulator 112 is, for example, movable through all six Cartesian degrees of freedom, five or fewer Cartesian degrees of freedom, etc.

In some implementations, mechanical or control constraints restrict the manipulator 112 to move the surgical instrument 108 around a particular center of motion that stays stationary with reference to the body of the patient 10. This center of motion is typically located proximate a location at which the surgical instrument 108 enters the body of the patient 10, e.g., at some point along the entry guide 110, such as the midpoint of the body wall.

The manipulator 112 includes a joint 114 and an elongated spar 116 supporting the instrument carriage 106 and the entry guide 110. The instrument carriage 106 is movably mounted to the spar 116 and, in particular, is movable along the length of the spar 116 while the entry guide 110 is held fixed such that the surgical instrument 108 can be translated along an insertion axis relative to the body of the patient 10. The joint 114 is, for example, an adjusting joint operable to reposition the surgical instrument 108 at a desired angular orientation about the center of motion. Movement of the instrument carriage 106 along the spar 116 repositions the surgical instrument at a desired insertion point through the center of motion. The manipulator 112 includes, for example, teleoperated actuators (not shown) operable to the move the surgical instrument 108 as a whole, as compared to the teleoperated actuators housed in the instrument carriage 106, which move only the end effector the surgical instrument 108 or other individual instrument components. The manipulator 112 is illustrative of both manipulators that are configured to constrain the remote center of motion by fixed intersecting manipulator joint axes (hardware-constrained remote center of motion) and manipulators controlled by software to keep a defined remote center of motion fixed in space (software-constrained remote center of motion).

The surgical instrument corresponds to a medical device for insertion into a patient's body and use in performing surgical or diagnostic operations. A surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with implementations of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path.

Surgical instruments appropriate for use in one or more implementations of the present disclosure may control their end effectors with one or more tensioning elements driven. The one or more tensioning elements include, for example, one or more rods and/or flexible cables. In some examples, rods, which may be in the form of tubes, may be combined with cables to provide a pull, push, or combined "push/pull" control of the end effector, with the cables providing flexible sections as required. A typical elongate shaft for a surgical instrument is, for example, five to eight millimeters in diameter. The diminutive scale of the mechanisms in the surgical instrument creates unique mechanical conditions and issues with the construction of these mechanisms that are unlike those found in similar mechanisms constructed at a larger scale, because forces and strengths of materials do not scale at the same rate as the size of the mechanisms. The tensioning elements are configured to fit within the elongate shaft of the surgical instrument and be able to control the end effector through the wrist joint. The cables may be manufactured from a variety of metal (e.g., tungsten or stainless steel) or polymer (e.g., high molecular weight polyethylene) materials.

Example Surgical Instruments

FIG. 2A illustrates an example of the surgical instrument 108. The surgical instrument 108 includes a distal portion 120 and a proximal drive assembly 122 coupled to one another by an elongate shaft 124 defining an internal bore. The drive assembly 122 includes a housing 125 supporting an input device 126. The input device 126 includes the instrument control surface 127. The input device 126 facilitates controlled adjustment of the distal end component of the surgical instrument 108 via a tensioning element extending along the internal bore of the elongate shaft 124.

The control surface 127 provides mechanical connections to the other control features of the surgical instrument 108. During a surgical procedure, the control surface 127 couples to the instrument carriage 106 (see FIG. 1), which controls the surgical instrument 108, as described herein. The distal portion 120 of the surgical instrument 108 includes an end effector 128. The end effector 128 is, for example, a forceps driven to grasp tissue of the patient 10 during the surgical procedure. While depicted as forceps, in some cases, the end effector 128 a needle driver, a cautery device, a cutting tool, an imaging device (e.g., an endoscope or ultrasound probe), or a combined device that includes a combination of two or more various tools and imaging devices. Further, in the illustrated implementation, the end effector 128 are coupled to the elongate shaft 124 by a wrist joint 130, which allows the orientation of the forceps to be manipulated with reference to the elongate shaft 124.

The bottom view of surgical instrument 108 shown in FIG. 2B illustrates the control surface 127 of the input device 126. As shown, the control surface 127 includes a set of five steering inputs 132, each of which governs a different aspect of movement by wrist joint 130 and end effector 128. When the control surface 127 is coupled to the instrument carriage 106, each of the steering inputs 132 interfaces with a corresponding actuator. The steering inputs 132 are configured to form a direct mechanical engagement with respective rotary actuators, e.g., servo motors, of the instrument carriage 106. The actuators are selectively operated to selectively drive the steering inputs 132.

Figure 3:
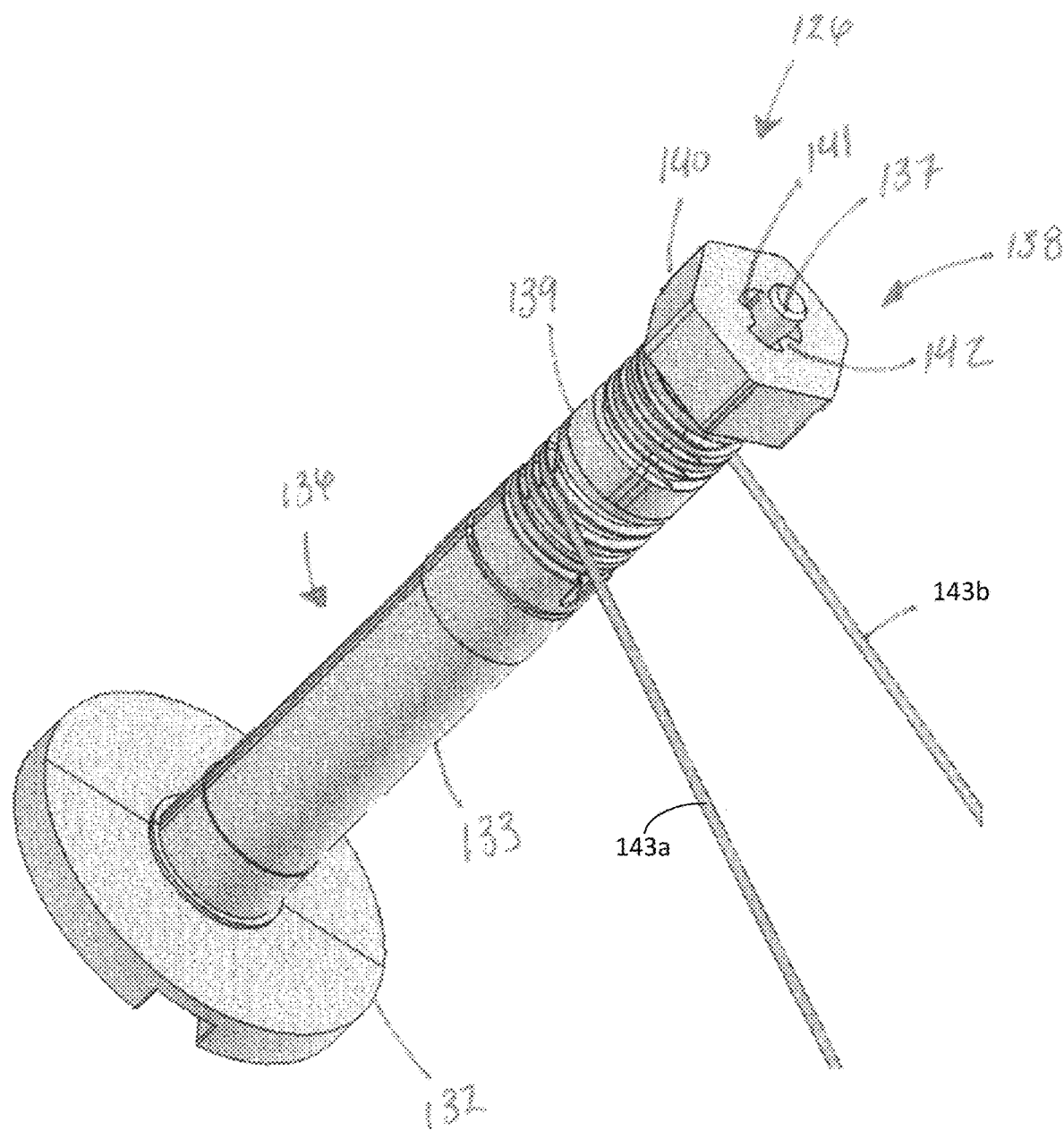
FIG. 3 is a perspective view of the input device of FIG. 2A carrying a tensioning element.

Each of the steering inputs 132 is part of a drive shaft, e.g., the first drive shaft 136 shown in FIG. 3, that, when driven, operates a tensioning element controlling movement of the end effector 128. Each steering input 132 is, in some cases, driven to operate two or more tensioning elements, e.g., the tensioning element 143a, 143b shown in FIG. 3. Preloads are applied to the tensioning elements 143a, 143b so that output motion of the end effector 128 is more rapidly responsive to input torques applied to the steering inputs 132. In addition, the preloads are applied to the tensioning elements 143a, 143b so that the motion of the end effector 128 can be more precisely controlled. As described herein, these preloads can be precisely applied during assembly and manufacture of the surgical instrument 108.

Additional or fewer steering inputs 132 are present in different implementations. In this regard, the surgical instrument may include fewer or more tensioning elements. In some implementations, while FIG. 2B illustrates particular configurations of the steering inputs 132, other suitable configurations for power transmission are used, e.g., indirect mechanical couplings including speed and/or torque converters, fluid couplings, and/or electrical couplings.

Figure 4:
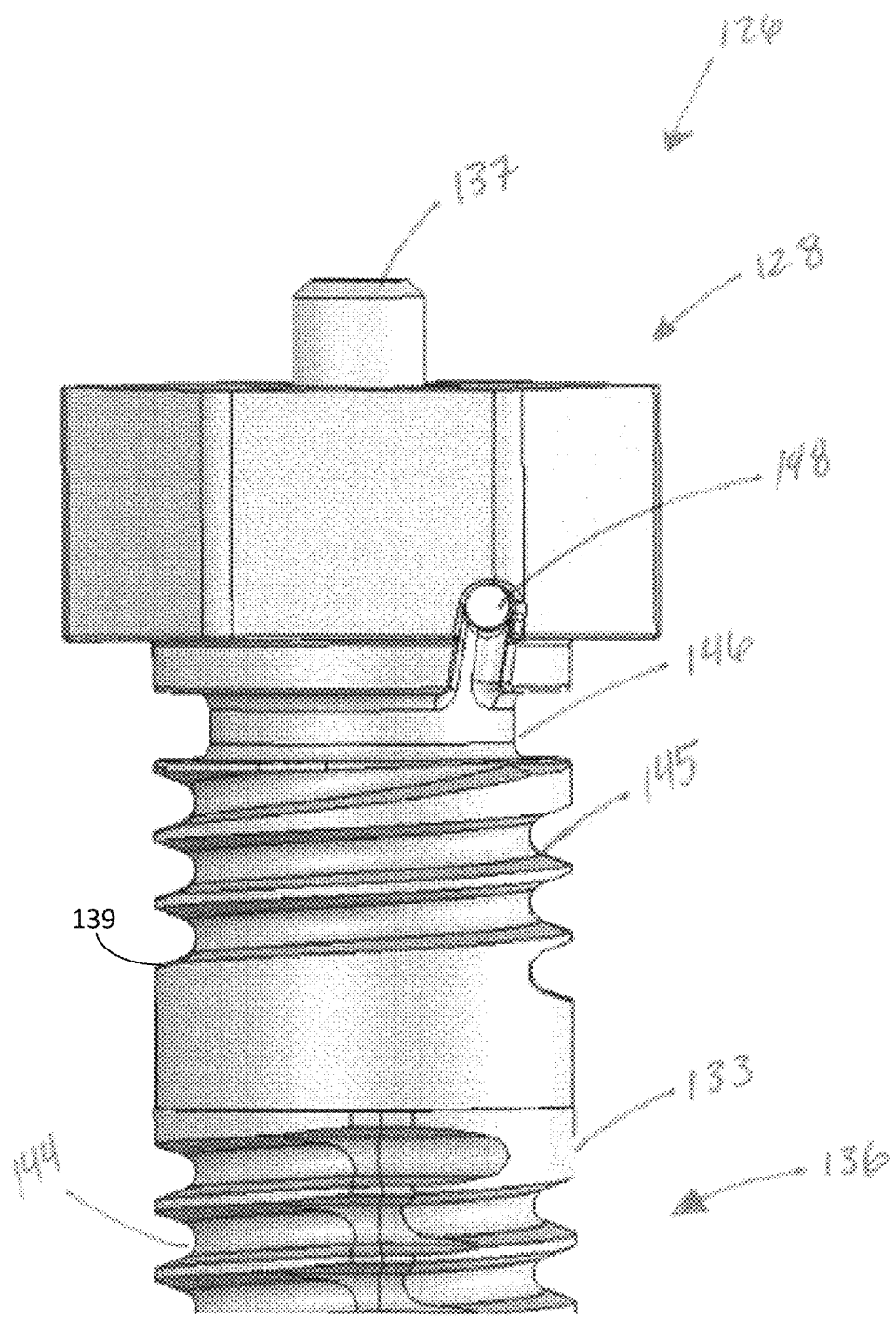
FIG. 4 is an enlarged partial side view of the input device of FIG. 2A.

FIGS. 3 and 4 illustrate an isolated portion of the input device 126. The first drive shaft 136 and the second draft shaft 138 are separate and independent structures, illustrated here in a releasable engaged state. The first drive shaft 136 and the second drive shaft 138 include features to enable the drive shafts 136, 138 to be releasably engaged. When the first drive shaft 136 and the second drive shaft 138 are in an engaged state, they can be driven relative to one another to disengage them from one another, thereby placing them in a disengaged state. While in the engaged state, relative rotation between the first drive shaft 136 and the second draft shaft 138 is inhibited, e.g., the first drive shaft 136 and the second drive shaft 138 are not rotatable relative to another and are rotationally coupled to one another. The first drive shaft 136 and the second drive shaft 138 are in the engaged state when the surgical instrument 108 is fully assembled. While in the disengaged state, the first drive shaft 136 and the second drive shaft 138 are permitted to rotate relative to one another. The first and second drive shafts 136, 138 are in the disengaged state during a portion of the process to facilitate assembly and manufacture the surgical instrument 108.

The first drive shaft 136 includes the disk-shaped steering input 132 and a first rotatable cylinder 133 extending outward from the steering input 132 along an axis of rotation of the steering input 132. The first drive shaft 136 further includes a support stem 137 extending telescopically from a bore of the first rotatable cylinder 133. In this example, the steering input 132 and the first rotatable cylinder 133 are thermoplastic parts (e.g., nylon or polycarbonate) that are overmolded around the metallic support stem 137.

The second draft shaft 138 is a contiguous and monolithic bolt-shaped structure including a second rotatable cylinder 139 and a flat-top, polygonal head 140. The head is hexagonal in this example, but other configurations are also envisioned. A central bore 141 extends longitudinally through both the second rotatable cylinder 139 and the head 140. Inwardly projecting prongs 142 located in the region of the head 140 extend from the wall of bore 141 towards the center of the second draft shaft 138 to surround the support stem 137 of the first drive shaft 136 (see FIG. 3). When the first drive shaft 136 and the second draft shaft 138 are disengaged, the first and second drive shafts 136, 138 are independently rotatable relative to one another. The support stem 137 functions as a spindle that provides a central axis of rotation for the rotation of the first and second drive shafts 136, 138. Additional features of the first drive shaft 136 and the second draft shaft 138 are discussed below with reference to FIGS. 5-7B.

With continued reference to FIG. 3, input device 126 carries a tensioning element 143a and a tensioning element 143b. The tensioning elements 143a, 143b are fixed to the first drive shaft 136 and the second draft shaft 138 by friction couplings. The tensioning elements 143a, 143b are, for example, fixed to the rotatable cylinders 133, 139, respectively.

In some implementations, the tensioning elements 143a, 143b are tightly wound around the rotatable cylinders 133, 139 for multiple revolutions to provide sufficient surface friction to maintain the couplings intact. Both the first drive shaft 136 and the second draft shaft 138 include outwardly facing helical grooves 144, 145 along outer surfaces of the rotatable cylinders 133, 139 to guide the winding of the ends of the tensioning elements 143a, 143b around the drive shafts 136, 138 (see FIG. 4).

The second draft shaft 138 further includes an outwardly facing spool 146 and a tortuous path 148 (see FIG. 4). The spool 146 is provided in the form of a channel of significantly larger width than that of helical grooves 144, so as to support multiple overlapping windings of the tensioning elements 143a, 143b. The tortuous path 148 extends through the second draft shaft 138 in a direction at or near a right angle (e.g., perpendicular) to the longitudinal axis of the second drive shaft 138. The tortuous path 148 includes two or more sharp bends traversable by the tensioning element 143b to further enhance the surface friction with the second draft shaft 138.

During assembly, the tensioning element 143b is first guided through the tortuous path 148, and then wrapped over itself several times in the spool 146 before being routed into helical grooves 144. The tensioning element 143b partially wraps and releases itself from helical grooves 144 as the second draft shaft 138 rotates, but the windings secured in the spool 146 remain fixed in place. The spool 146 and tortuous path 148 are features that facilitate a frictional coupling between the tensioning element 143b and the second drive shaft 138. This frictional coupling enables the use of the tensioning element 143b without added end attachments (e.g., crimps), which further simplifies manufacturing and installation processes. Such features are enable the use of polymer cables, which, as noted above, may be preferred in some implementations. While not presently shown and described in detail, the first drive shaft 136 may also be provided with substantially similar features as the second draft shaft 138 to facilitate a secure frictional coupling with the tensioning element 143a.

The tensioning elements 143a, 143b, at their distal ends, are each coupled to a component at a distal end of the surgical instrument 108, e.g., a distal end component. The tensioning elements 143a, 143b are coupled to the distal end component in a manner to cause motion in a degree of freedom associated with the end effector 128. Motion in a first direction along the degree of freedom occurs when a tension is applied to the tensioning element 143a, and motion in a second direction along the degree of freedom occurs when a tension is applied to the tensioning element 143b. During a surgical procedure, the tensioning elements 143a, 143b are driven to move the end effector 128 to desired positions and orientations to perform operations on the tissue of the patient. As described herein, additional tensioning elements and additional input devices may be present to enable motion of the end effector 128 in multiple directions in multiple degrees of freedom.

The distal end component is, for example, the end effector 128. The tensioning elements 143a, 143b are each attached to a joint of the end effector 128 such that the tensioning elements 143a, 143b, when driven, actuates the end effector 128 to move the end effector 128 in a single degree of freedom. If the end effector 128 is a forceps, the tensioning elements 143a, 143b, when driven, open and close the jaws of the forceps.

Alternatively, rather than being directly connected to the end effector 128, the distal end component is a mechanism system coupled to the end effector. The distal end component is, for example, the wrist joint 130. The tensioning elements 143a, 143b are connected to the wrist joint 130 such that the tensioning elements 143a, 143b, when driven, move the end effector 128 in its entirety.

The tensioning elements 143a, 143b are coupled to one another such that a tension in one of the tensioning elements 143a, 143b is transmitted at least in part to the other of the tensioning elements 143a, 143b. In some implementations, the tensioning element 143a, 143b are coupled to one another through the distal end component. When a tension is applied to the tensioning element 143a, the motion of the distal end component causes a corresponding decrease in tension in the tensioning element 143b. Similarly, when a tension is applied to the tensioning element 143b, the motion of the distal end component causes a corresponding decrease in tension in the tensioning element 143a.

In alternative examples, the tensioning elements 143a, 143b are coupled to one another because the tensioning elements 143a, 143b are part of a continuous cable extending from the input device 126 to the end effector of the surgical instrument 108 and back to the input device. A first end of the tensioning element is attached to the first drive shaft 136, and a second end of the tensioning element is attached to the second draft shaft 138. The portion between the input device 126 and the distal end component forms the tensioning element 143a, and the portion between the input device 126 and the end effector forms the tensioning element 143b. The continuous cable is routed through the distal end component. In this regard, both the tensioning elements 143a, 143b are coupled to the distal end component such that the tensioning element 143a, when driven, causes motion in a first direction in the degree of freedom and the tensioning element 143b, when driven, causes motion in a second direction in the degree of freedom.

Though only a short section is shown, portions of the tensioning elements 143a, 143b distal to the portion depicted in FIG. 3 extend into the internal bore of the elongate shaft 124 of the surgical instrument 108. As described above, the tensioning element 143a, 143b traverses the internal bore and couples to the end effector 128 of the surgical instrument 108. Power provided by an actuator of the instrument carriage 106 is transmitted to the first drive shaft 136 and the second drive shaft 138 via steering input 132, causing the input device 126 to rotate. With the first and second drive shafts 136, 138 of the input device 126 in the engaged state, the rotary motion of the first drive shaft 136 is directly transferred to the second draft shaft 138. Shared rotation of the first drive shaft 136 and the second draft shaft 138 causes the tensioning elements 143a, 143b to equally release from or further entwine these components. As shown in FIG. 3, the tensioning elements 143a, 143b are wound about the rotatable cylinders 133, 139 in opposite directions, such that their simultaneous rotation in a clockwise direction causes the tensioning element 143b to release from the second drive shaft 138 while the tensioning element 143a becomes further wound about the first drive shaft 136, and vice versa with counter-clockwise rotation. The distal end component is driven as the tensioning elements 143a, 143b are selectively wound about the rotatable cylinders 133, 139.

In some examples, preloads are applied to the tensioning elements 143a, 143b. The preloads correspond to tension forces applied to the tensioning elements 143a, 143b that are present even when the tensioning elements 143a, 143b are not being driven by an external device, e.g., by actuators of the instrument carriage 106. As described herein with respect to an assembly process 500, the preloads can be applied during the assembly process 500 and then maintained such that the preloads are present during use for a surgical procedure.

Example Input Device Engagement Mechanisms

Figure 5:
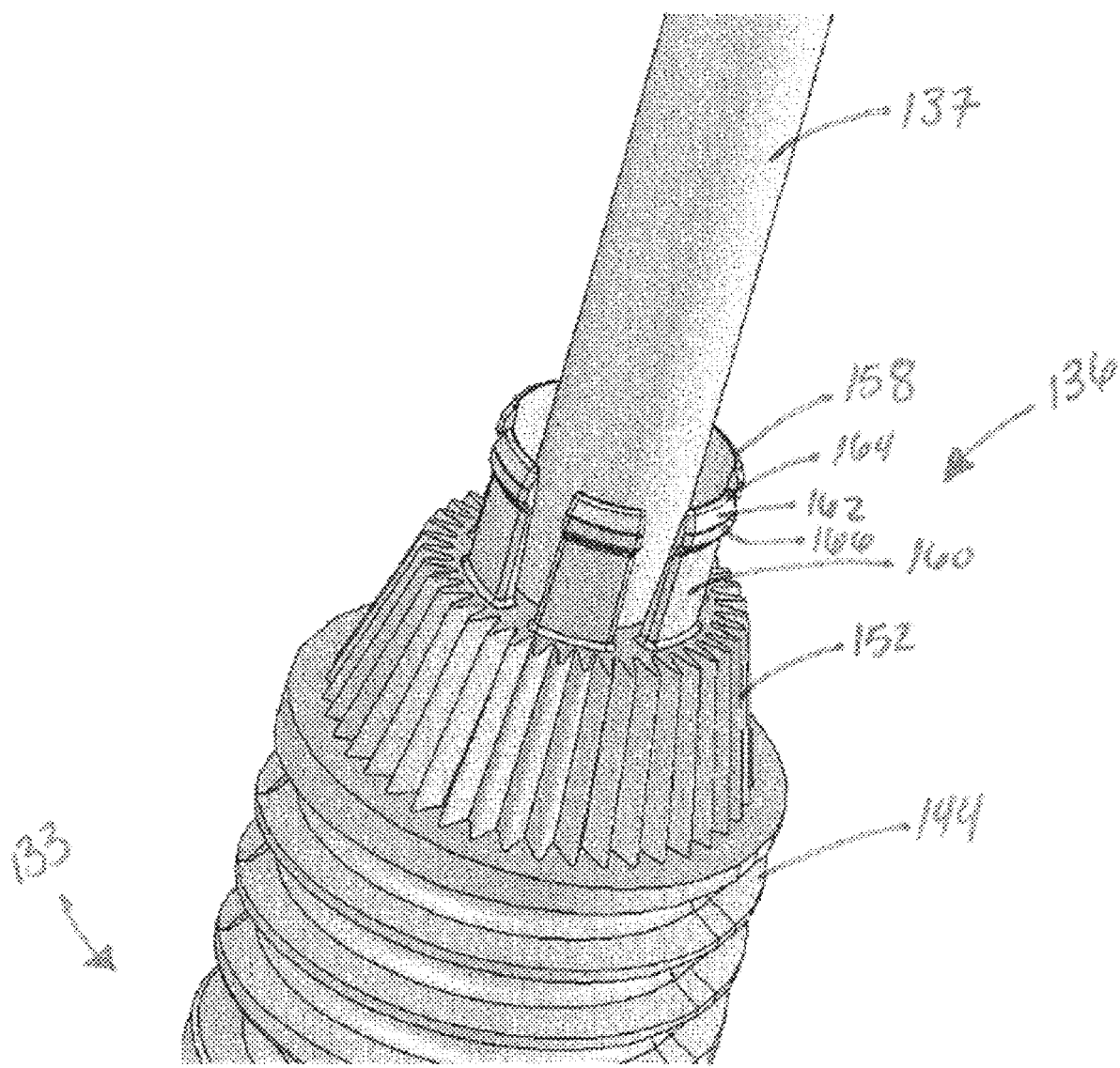
FIG. 5 is a perspective view of a drive shaft of the input device of FIG. 2A.
Figure 6B:
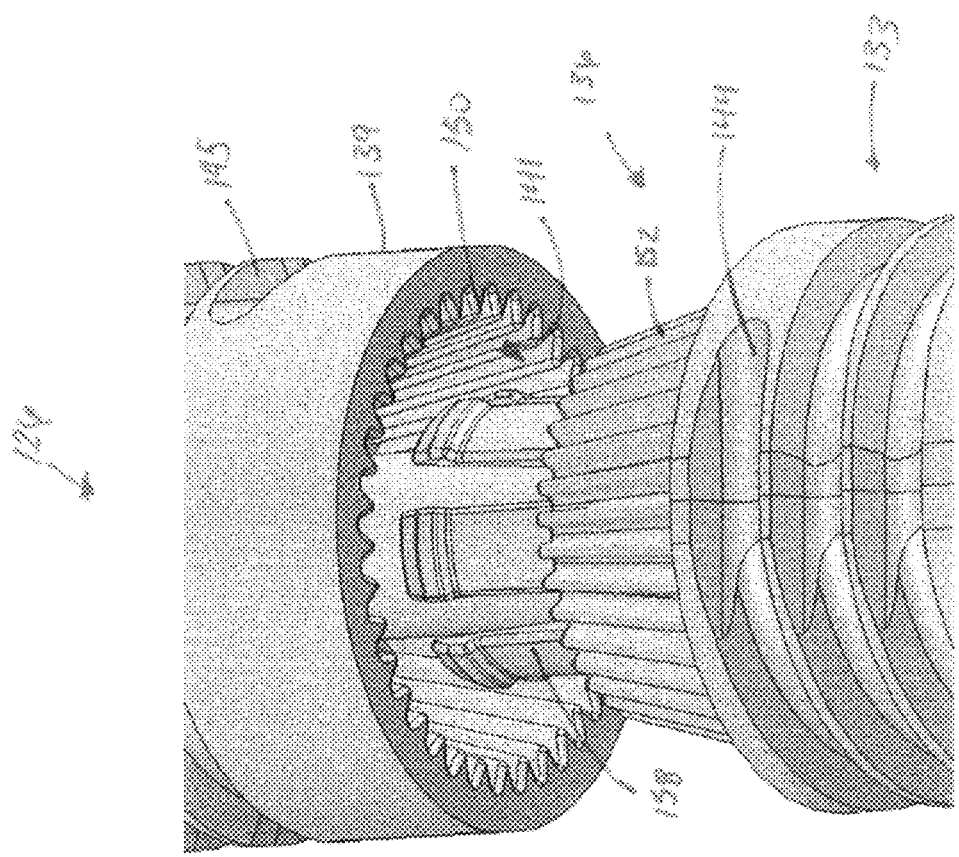
FIGS. 6A and 6B are perspective top and bottom views of the input device of FIG. 2A illustrating a second drive shaft being lowered into a first drive shaft.
Figure 6A:
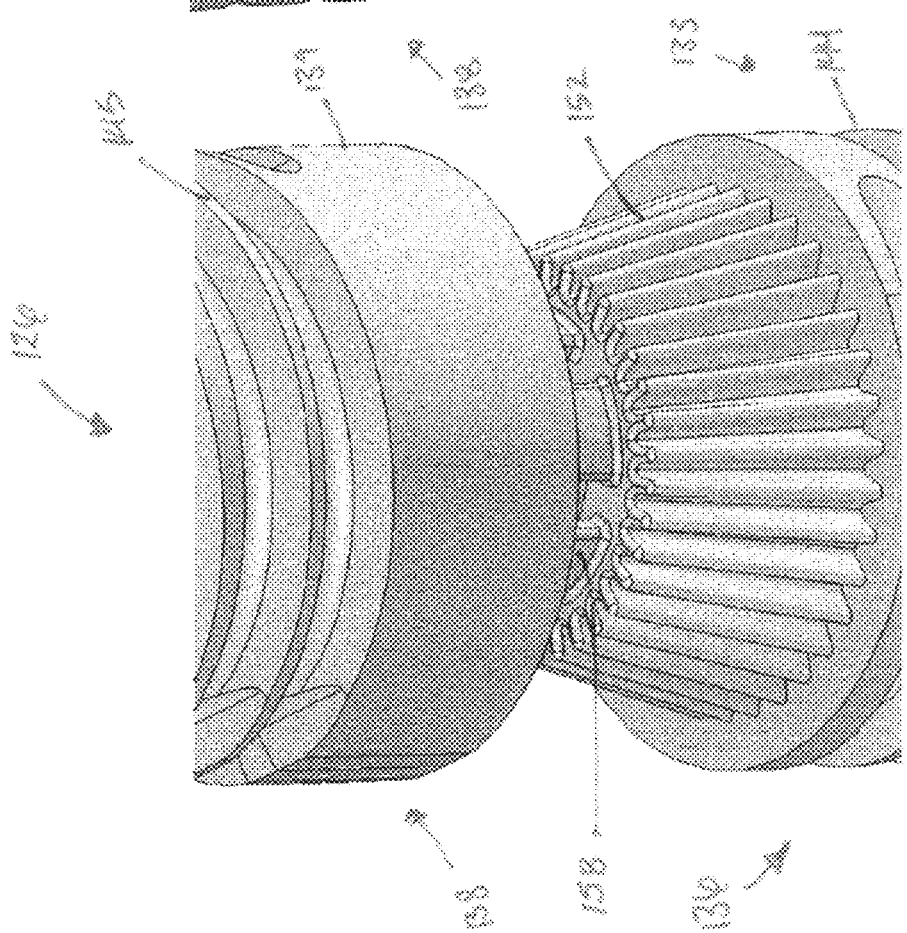
Figure 7B:
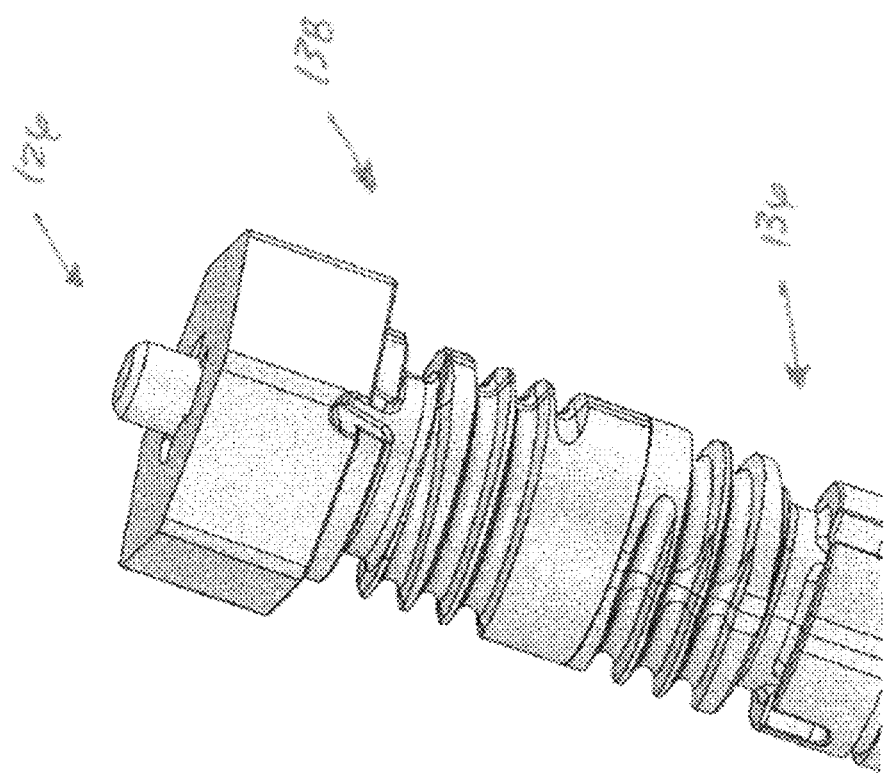
FIGS. 7A and 7B are perspective views of the input device of FIG. 2A illustrating the second drive shaft and the first drive shaft in a disengaged state and an engaged state, respectively.
Figure 7A:
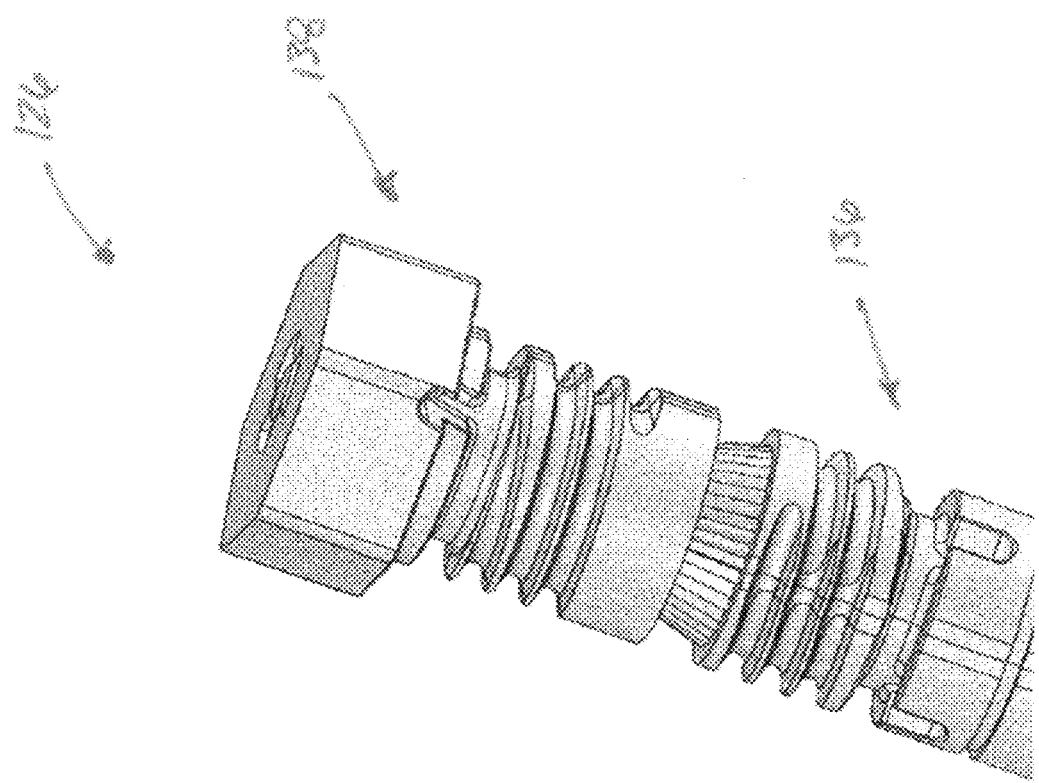

The first drive shaft 136 and the second drive shaft 138 can be engaged to one another through a variety of engagement mechanisms. FIGS. 5, 6A, and 6B depict an example engagement mechanism including features that enable engagement of the first drive shaft 136 and the second drive shaft 138 of the input device 126 in accordance to some implementations. In other implementations described herein, the engagement mechanism includes other features to enable the engagement between a first drive shaft and a second drive shaft.

In the examples of FIGS. 5, 6A, and 6B, an engagement mechanism engages the first drive shaft 136 to the second drive shaft 138 to inhibit relative rotation and relative longitudinal translation between the drive shafts 136, 138. The engagement mechanism includes diametrically spaced vertical splines 150 (see FIG. 6B). The splines 150 are located in the region of the second rotatable cylinder 139, projecting inwardly from the wall, thereby defining the bore 141 through the second rotatable cylinder 139 (see FIG. 6B). As shown, the splines 150 are radially tapered along the longitudinal direction of the second draft shaft 138, such that the degree of inward protrusion decreases along the length of the second drive shaft 138 in a downward direction (i.e., the longitudinal direction leading from head 140 to the second rotatable cylinder 139). Thus, the vertical splines 150 define a reverse-frustoconical cavity.

The engagement mechanism further includes vertical splines 152. The first rotatable cylinder 133 of the first drive shaft 136 also includes the vertical splines 152. The splines 152 are diametrically spaced along an outer surface of the first rotatable cylinder 133, located just above helical grooves 144. The splines 152 of the first drive shaft 136 are specifically designed to engage the splines 150 of the second drive shaft 138. The splines 152 are also radially tapered, but in an opposite (i.e., upward) direction as the direction of the taper of the splines 150.

The splines 152 form a frustoconical structure on the first drive shaft 136. The frustoconical structure is appropriately sized to be accommodated by the reverse-frustoconical cavity of the central bore 141 of the second drive shaft 138. When the second draft shaft 138 is fitted over and pressed down upon the first drive shaft 136, the splines 150 and 152 form a keyed interlocking mesh inhibiting or entirely preventing relative movement between the splines 150 and the splines 152, e.g., relative rotation between the splines 150 and the splines 152. In the engaged state of the drive shafts 136, 138, the engagement mechanism formed from the splines 152 and the vertical splines 150 is configured to inhibit relative rotation of the first drive shaft 136 and the second drive shaft 138. The splines 150, 152, when engaged, rotationally lock the first drive shaft 136 and the second drive shaft 138 together.

In some examples, the conical nature of the respective splines can ease the meshing action between them, and may also reduce wear in certain configurations and conditions. Further, as shown particularly well in FIGS. 6A and 6B, the splines 150 and 152 are provided with relatively smooth chamfered edges that serve the dual purpose of inhibiting stress concentrations and also providing lead-in surfaces angled from the vertical direction of the splines 150, 152. The lead-in function of the chamfered edges allows the splines to self-correct slight misalignments by sliding passed one another into engagement under a slight downward force. This self-correction feature of the mating splines is one of several features that simplifies assembly, enabling automation.

The engagement mechanism further includes another engagement mechanism that inhibits relative translation of the first drive shaft 136 and the second drive shaft 138 along a longitudinal axis of the input device 126, e.g., an axis of rotation of the input device 126. The first drive shaft 136 includes diametrically spaced snap fingers 158 located atop the splines 152. The snap fingers 158 are provided to lock the second drive shaft 138 onto the first drive shaft 136 in the vertical direction to inhibit unintentional disengagement during use. As noted below, while the snap fingers 158 may securely hold the second drive shaft 138 in place on the first drive shaft 136, they may also permit its release in response to sufficient upward force. The snap fingers 158 may provide a quick coupling operable without special tools or additional fasteners that may prohibit unintentional release of the second drive shaft 138 from the first drive shaft 136 while also permitting its intentional release. Thus, the snap fingers 158 may simplify the process to assemble and manufacture the surgical instrument 108.

In this example, each of snap fingers 158 includes an elastic stem 160 and a lip 162 projecting radially outward from an upper end of the elastic stem 160 to engage an undercut ridge (not shown) along bore 141 of the second draft shaft 138. When the protruding lips of the snap fingers 158 meet the ridge under a downward external force, the elastic stems 160 are pressed inward until the lips 162 snap past the ridge, allowing the elastic stems 160 to recover to their initial position. The protruding lips 162 then bear against the ridge to resist vertical movement between the first drive shaft 136 and the second drive shaft 138. Each of lips 162 features both upper and lower beveled edges 164, 166. The upper beveled edge 164 facilitates sliding contact with the ridge as the second draft shaft 138 is pushed downward relative to the first drive shaft 136 to place the first and second drive shafts 136, 138 in the engaged state. The lower beveled edge 166 facilitates sliding contact with the ridge as the second draft shaft 138 is pulled upward relative to the first drive shaft 136 to release the first and second drive shafts 136, 138 from the engaged state.

As noted above, the first drive shaft 136 and the second draft shaft 138 are separate and independent structures capable of transitioning between the engaged state (see FIG. 7B), where relative rotation between them is inhibited, and the released or disengaged state (see FIG. 7A), where relative rotation between them is freely permitted. The first drive shaft 136 and the second draft shaft 138 are placed in the engaged state prior to use in order to facilitate push/pull operation of the end effector via the tensioning elements 143a, 143b, as described above. These components are placed in the disengaged state to facilitate tuning or pre-tensioning of the tensioning elements 143a, 143b. Assembly and configuring the surgical instrument 108 can include an operation to pre-tension the tensioning elements 143a, 143b so that the wrist joint 130 and the end effector 128 are accurately and rapidly responsive to rotation of the first drive shaft 136 and the second draft shaft 138, and so that the wrist joint 130 and the end effector 128 can be precisely controlled during a surgical operation.

While FIGS. 3-7B depict the input device 126 in accordance to some implementations, engagement mechanisms for input devices may vary in other implementations. FIG. 8A depicts an example of an input device 200 including a first drive shaft 204 and a second drive shaft 206 rotationally coupled to the first drive shaft 204. The first drive shaft 204 can be rotatably mounted to a housing of a drive assembly, e.g., the drive assembly 122, with a steering input 210 supported within a base of the drive assembly. The first drive shaft 204 includes a first rotatable cylinder 214, and the second drive shaft 206 includes a second rotatable cylinder 216 rotationally coupled to the first rotatable cylinder 214.

The input device 200 includes an engagement mechanism that differs from the engagement mechanism for the input device 126. The first drive shaft 204 and the second drive shaft 206 are illustrated in FIG. 8A in a disengaged state such that relative rotation of the first drive shaft 204 and the second drive shaft 206 is permitted. The first drive shaft 204 and the second drive shaft 206 are illustrated in FIG. 8B in an engaged state, such that the rotation of the first drive shaft 204 guided by the mounting hardware of the housing of the drive assembly imparts identical motion to the second drive shaft 206.

The engagement mechanism of the input device 200 includes a taper friction fit between the first drive shaft 204 and the second drive shaft 206 that inhibits relative rotation between them at the torques produced by tensions on the first and second drive shafts 204, 206. The engagement mechanism is formed by a lower portion 220 of a central bore 222 of the second drive shaft 206 and a support stem 224 of the first drive shaft 204. As shown in FIG. 8B, the lower portion 220 of the central bore 222 of the second drive shaft 206 and the support stem 224 of the first drive shaft 204 are mutually sized for surface-to-surface contact. The support stem 224 extends into the central bore 222, and the walls defining the lower portion 220 of the central bore 222 contact the support stem 224 to form the friction fit between the first drive shaft 204 and the second drive shaft 206. In some examples, the mating surfaces of support stem 224 and lower portion 220 of the central bore 222 are rounded and smooth, forming a frictional coupling that is both keyless and unthreaded. In this regard, the first and second drive shafts 204, 206 can transition from the disengaged state to the engaged state by simply imparting a downward vertical force on the second drive shaft 206, thereby moving the second drive shaft 206 toward the first drive shaft 204 and causing the support stem 224 to engage the lower portion 220 of the central bore 222. The lower portion 220 of the central bore 222 and the support stem 224, when engaged, may enable the first and second drive shafts 204, 206 to be properly aligned such that additional alignment operations may not be necessary. Such an engagement between the first and second drive shafts 204, 206 can simplify the assembly and pre-tensioning processes for the tensioning elements (not shown) engaged to the first and second rotatable cylinders 214, 216 of the first and second drive shafts 204, 206, respectively.

In some examples, the mating surfaces of the support stem 224 and the lower portion 220 of the central bore 222 are not only rounded, but also radially tapered. The support stem 224 and the lower portion of the central bore 222 are both, for example, frustoconically shaped. The radial tapering aspect permits the second drive shaft 206 to sit loosely on the support stem 224 of the first drive shaft 204 absent an external downward force that would cause the support stem 224 and the lower portion 220 of the central bore 222 to engage in a press fit that inhibit relative rotation of the first and second drive shafts 204, 206. In this regard, in such a disengaged state, the first and second drive shafts 204, 206 are independently rotatable along longitudinal axes of the first and second drive shafts 204, 206.

Radial tapering of these components further enables the taper friction fit to function as a self-locking engagement mechanism in which mating surfaces of the first and second drive shafts 204, 206 provide sufficient frictional force to prevent relative rotation between the first and second drive shafts 204, 206 under the forces/loads transmitted during a surgical procedure absent any external force. The engagement mechanism is formed by providing the mating surfaces of the drive shafts 204, 206 with a certain taper angle, thereby enabling the engagement mechanism to be self-locking. This self-locking taper angle is a function of several variables, including material properties, surface roughness, expected forces/loads, etc. In some implementations, the self-locking taper angle is less than about 1.5 degrees (e.g., about 1.49 degrees). With a self-locking engagement mechanism, the second drive shaft 206 is pressed down on the first drive shaft 204 to engage the two drive shafts 204, 206. The force to press the second drive shaft 206 is then removed without disturbing the frictional engagement between the drive shafts 204, 206. The self-locking engagement is maintained during use in a surgical procedure.

Examples Systems for Assembling Surgical Instruments

Figure 9A:
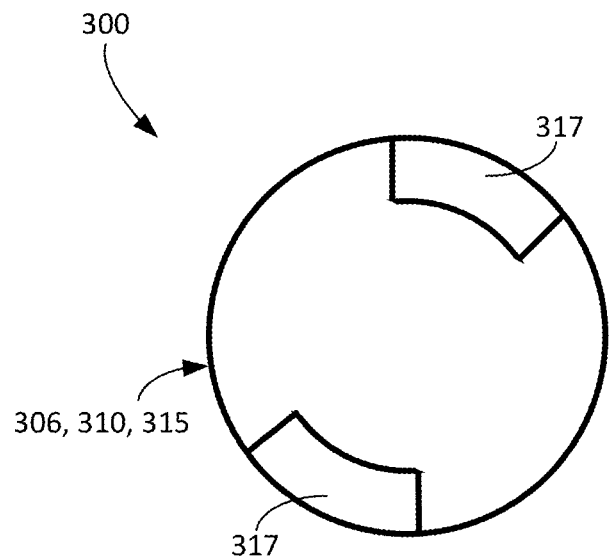
FIG. 9A is a top view of yet another example of an input device with drive shafts in a disengaged state.
Figure 9B:
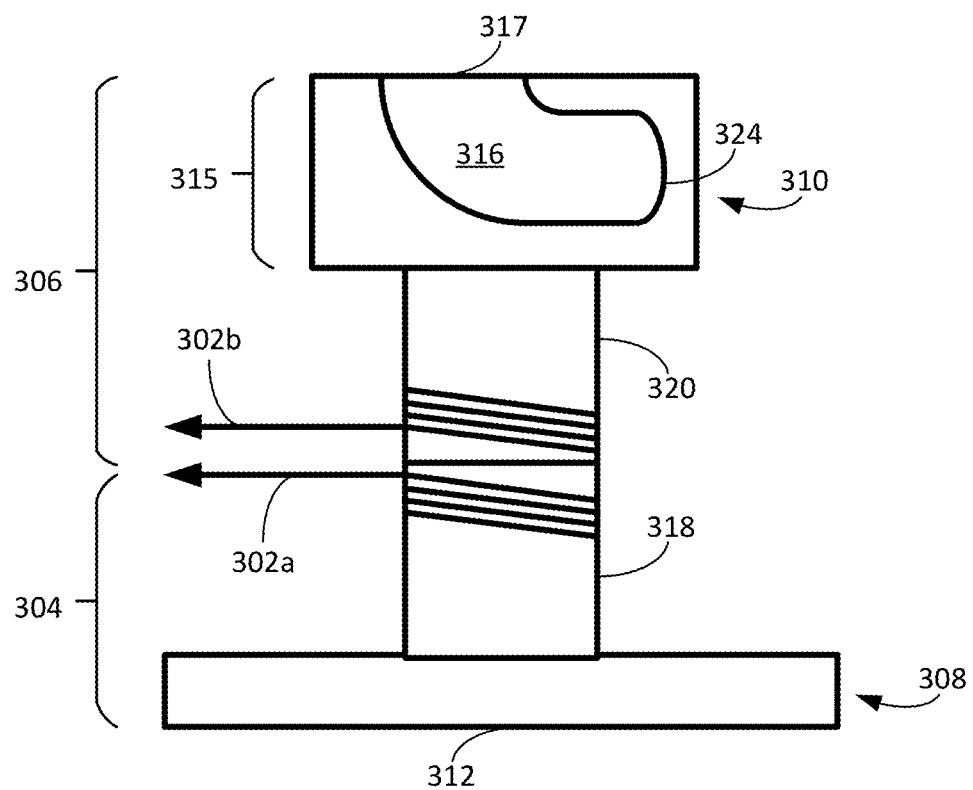
FIG. 9B is a side view of the input device of FIG. 9A.

To assemble the surgical instruments described herein, an assembly apparatus can be used to facilitate assembly of a surgical instrument. The surgical instrument may also include features that facilitate assembly of the surgical instrument. Specifically, the input device of the surgical instrument can include features to aid in assembling the surgical instrument. FIGS. 9A and 9B depict one example of an input device 300 that includes features that facilitate assembly of a surgical instrument. In particular, the input device 300 includes features to facilitate application of preloads to tensioning elements 302a, 302b attached to the input device 300. A first drive shaft 304 of the input device 300 includes a first drive input 308, and a second drive shaft 306 includes a second drive input 310. The first drive shaft 304 corresponds to, for example, the first drive shaft 136 or the first drive shaft 204, and the second drive shaft 306 corresponds to the second drive shaft 138 or the second drive shaft 206. Furthermore, the tensioning elements 302a, 302b are similar to the tensioning elements 143a, 143b described herein. Specifically, the tensioning elements 302a, 302b are coupled to one another and are coupled to the first and second rotatable cylinders 318, 320 of the first and second drive shafts 304, 306, respectively. The tensioning elements 302a, 302b, when driven, cause motion in a degree of freedom for an end effector to which the tensioning elements 302a, 302b are coupled. The tensioning element 302a, when driven, moves the end effector in a first direction in the degree of freedom, and the tensioning element 302b, when driven, moves the end effector in a second direction in the degree of freedom.

Figure 10:
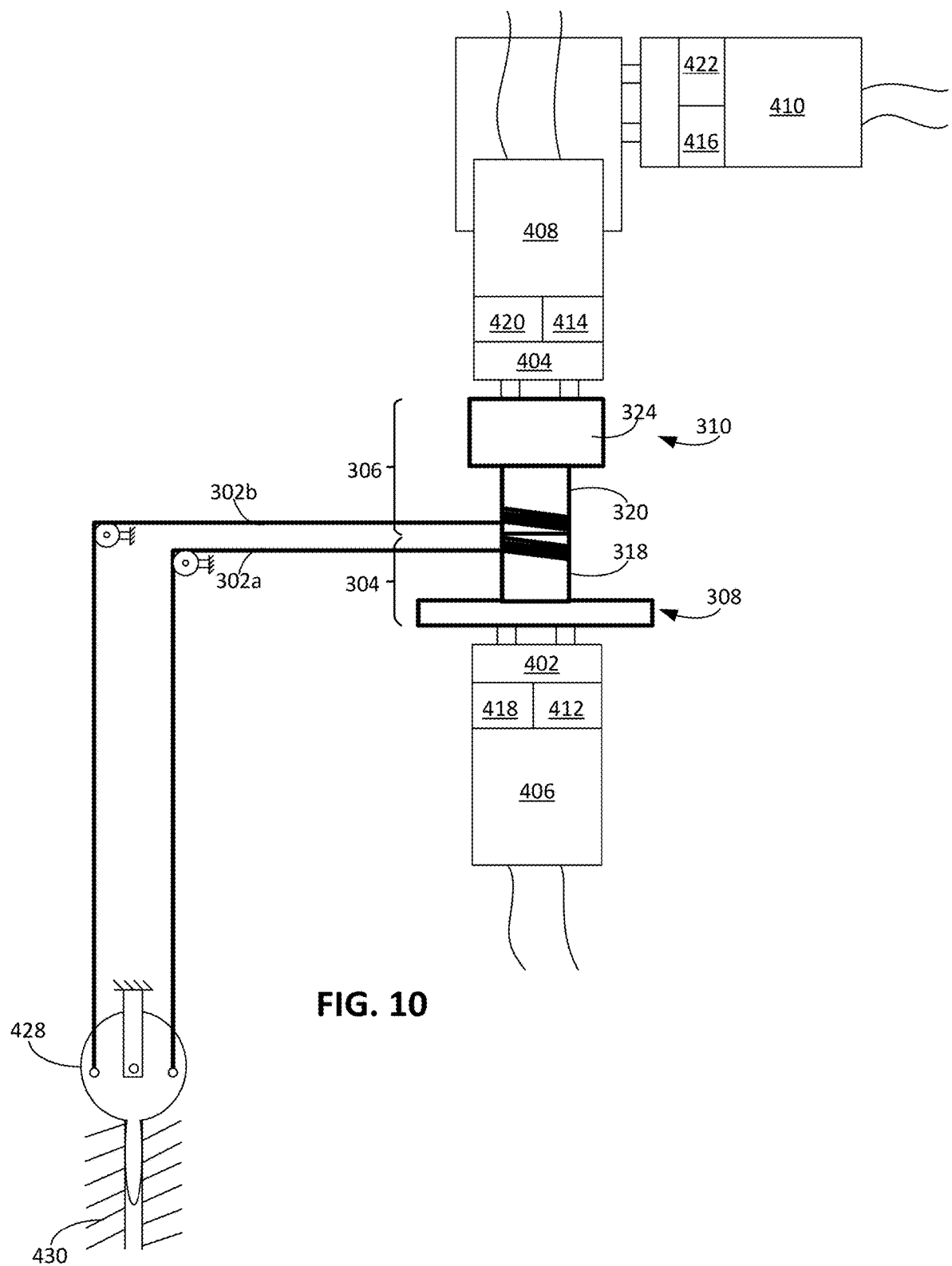
FIG. 10 is a functional diagram of an assembly apparatus engaged to an input device.

The first drive input 308 and the second drive input 310 are each configured to be driven by a corresponding actuator of an assembly apparatus 400 described with respect to FIG. 10. To apply the preloads, the first drive input 308 and the second drive input 310 are driven while the first drive shaft 304 and the second drive shaft 306 are in the disengaged state. In this regard, the tensioning element 302a increasingly wraps around a first rotatable cylinder 318 of the first drive shaft 304 when the first drive shaft 304 is driven relative to the second drive shaft 306. The tensioning element 302b increasingly wraps around a second rotatable cylinder 320 of the second drive shaft 306 when the second drive shaft 306 is rotated relative to the first drive shaft 304. A tension in one of the tensioning elements 302a, 302b caused by the drive shafts 304, 306 being driven is transmitted to the other the tensioning elements 302a, 302b.

The first and second drive inputs 308, 310 include features to facilitate engagement with the assembly apparatus 400. The first drive input 308 includes, for example, a steering input 312, e.g., similar to the steering input 132 and/or the steering input 210, and the second drive input 310 includes a head portion 315 with ramped recesses 316 and radial openings 317 connected to the ramped recesses 316. In this regard, as described herein, the steering input 312 is configured to engaged to a first actuator of the assembly apparatus, and the head portion 315 is configured to be engaged to a second actuator of the assembly apparatus.

Referring to FIG. 10, pre-tensioning of the tensioning elements 302a, 302b can be performed using the assembly apparatus 400. The assembly apparatus 400 is appropriately configured to independently rotate the first drive shaft 304 and the second drive shaft 306 of the input device 300 when the first drive shaft 304 and the second drive shaft 306 are in a disengaged state. As described herein with respect to the assembly process 500 depicted in FIG. 11, the assembly apparatus 400 is operated to apply pre-loads to tensioning elements 302a, 302b. The assembly apparatus 400 drives the first drive shaft 304 and the second drive shaft 306 to apply these preloads. The assembly apparatus 400 is operated to independently rotate the first drive shaft 304 and the second drive shaft 306 such that the tensioning elements 302a, 302b are driven by first and second rotatable cylinders 318, 320.

The assembly apparatus 400 includes a first drive mechanism 402 and a second drive mechanism 404. The first drive mechanism 402 is powered by a first motor 406, and the second drive mechanism 404 is powered by a second motor 408. The first drive shaft 304 is carried by the first drive mechanism 402, and the second draft shaft 306 is carried by the second drive mechanism 404. As discussed with respect to the assembly process 500, the two drive mechanisms 402, 404 can be used to pre-tension the tensioning elements 302a, 302b. The first motor 406 and the second motor 408, when driven, cause rotation of the first drive mechanism 402 and the second drive mechanism 404, respectively. In this regard, the first and second motors 406, 408 are activated to drive the tensioning elements 302a, 302b to apply the preloads to the tensioning elements 302a, 302b.

In some implementations, the assembly apparatus 400 further includes a third motor 410 that drives the second drive mechanism 404. The second drive mechanism 404 includes a drivetrain that enables the third motor 410, when driven, to cause axial motion of the second drive mechanism 404 along a longitudinal axis of the input device 300, e.g., a longitudinal axis of the second drive shaft 306. The second drive mechanism 404 moves axially from a first axial position in which the second drive mechanism 404 is not engaged with the second drive shaft 306 to a second axial position in which the second drive mechanism 404 is axially engaged with the second drive shaft 306.

In some implementations, the assembly apparatus 400 further includes encoders 412, 414, 416 to measure positions of the motors 406, 408, 410. Alternatively or additionally, the assembly apparatus 400 includes torque sensors 418, 420, 422 to measure the torques applied to the motors 406, 408, 410. As described with respect to the assembly process 500, the assembly apparatus 400, e.g., a controller of the assembly apparatus 400, can monitor the torques and the positions of the motors 406, 408, 410 while driving the tensioning elements 302a, 302b to the desired preload.

The first drive mechanism 402 and the second drive mechanism 404 can vary between implementations. In some cases, the first drive mechanism 402 corresponds to, for example, a mechanism similar to the instrument carriage 106. In this regard, the first drive mechanism 402 engages with the steering input 312 of the first drive shaft 304 such that rotation of the first drive mechanism 402 causes rotation of the steering input 312 and hence rotation of the first drive shaft 304.

Figure 11:
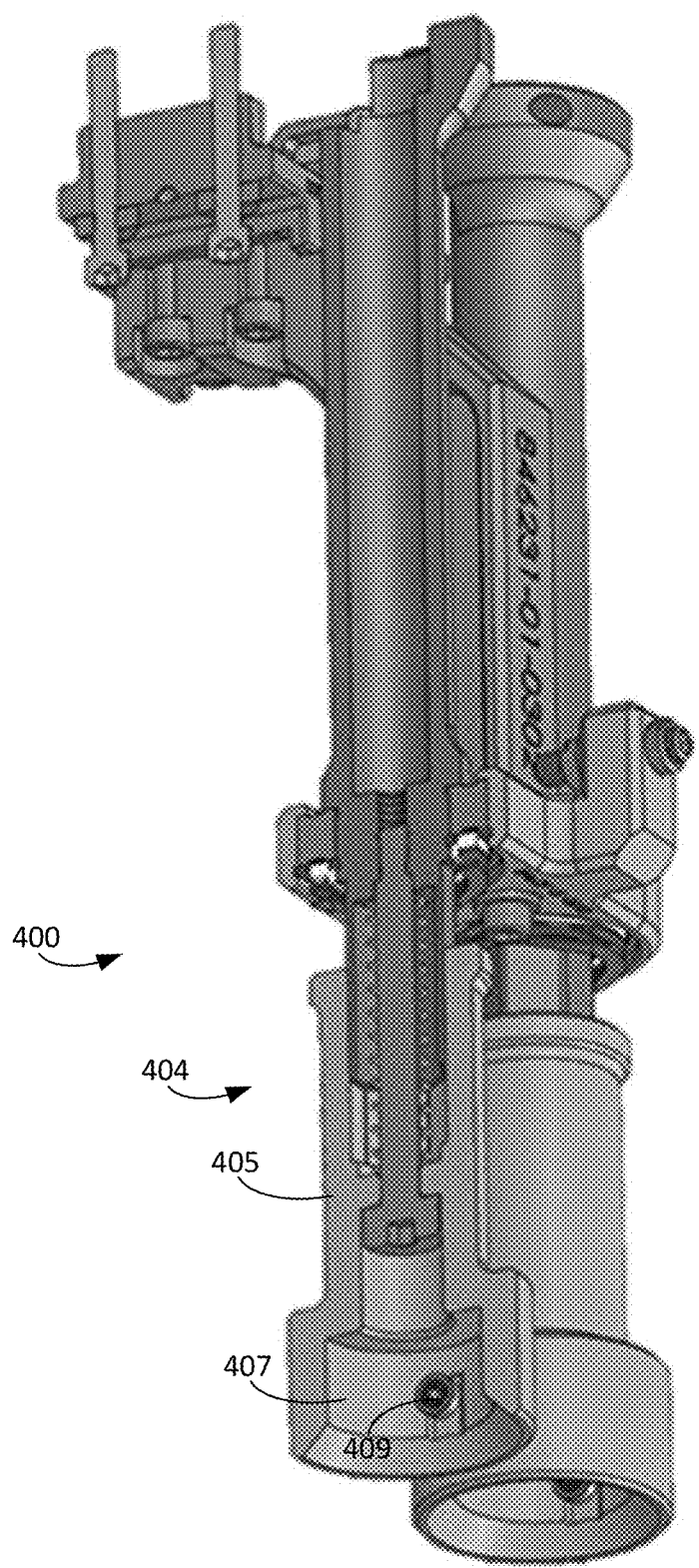
FIG. 11 is a perspective view of a portion of the assembly apparatus of FIG. 10.
Figure 12A:
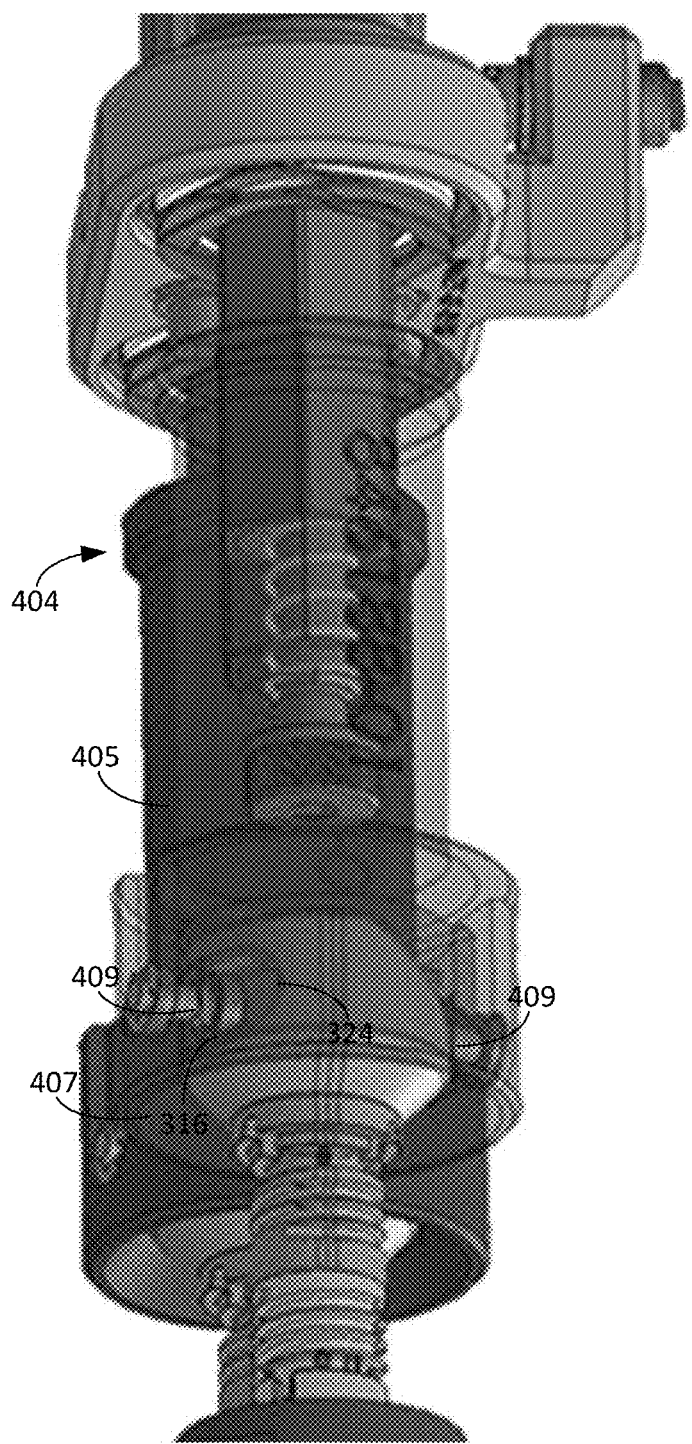
FIG. 12A is a perspective view of the assembly apparatus engaged to the input device.
Figure 12B:
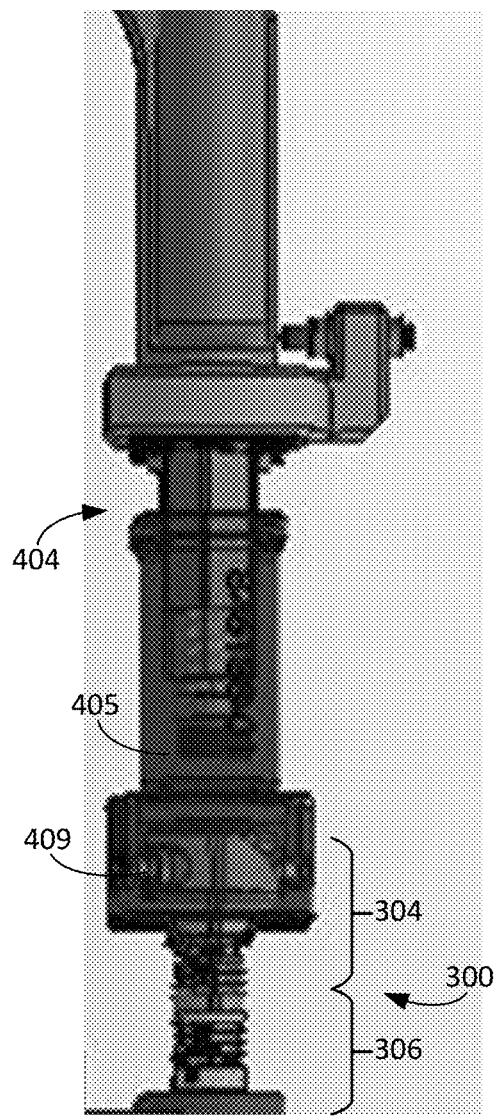
FIG. 12B is a side view of the assembly apparatus engaged to the input device.

FIG. 11 depicts an example of the second drive mechanism 404, and FIGS. 12A and 12B depict the second drive mechanism 404 engaged with the second drive shaft 306. The second drive mechanism 404 includes an arm 405 that is axially drivable along the longitudinal axis and that is rotatable about the longitudinal axis. The arm 405 defines a bore 407 to receive the second drive shaft 306, in particular, to receive the head portion 315 of the second drive shaft 306. The arm 405 axially engages with the head portion 315. Two bosses 409 are positioned within the bore 407 of the arm 405 and extend radially inward into the bore 407. During assembly, when the arm 405 is driven axially along the longitudinal axis by the third motor 410, the bosses 409 engage the ramped recesses 316. When the bosses 409 are within the ramped recesses 316, the second motor 408 is driven to rotate the arm 405. The bosses 409 thus also rotate relative to the ramped recesses 316, thereby travelling through the ramped recesses 316 until the bosses hit stops 324 at ends of the ramped recesses 316 (only one is shown in FIG. 9B). When the bosses 409 engage the stops 324, the arm 405 is rotationally coupled to the bosses 409 such that rotation of the arm 405 in a first direction toward the stops 324 causes a corresponding rotation of the second drive shaft 306. After the bosses 409 are engaged to the stops 324, the arm 405 is rotatable in a second direction opposite the first direction to disengage the bosses 409 from the stops 324. While two bosses 409 are shown, one, three, or more bosses may be present to engage the ramped recesses 316.

In some implementations, the two bosses 409 include bearings that interface with walls defining the ramped recesses 316. During rotation of the second drive shaft 306 prior to the second drive shaft 306 engaging the stops 324, the bearings can reduce the friction forces between the bosses 409 and the walls so that the friction forces do not inadvertently cause motion of the second drive shaft 306 before the bosses 409 engage the stops 324.

Example Assembly Processes

Figure 13:
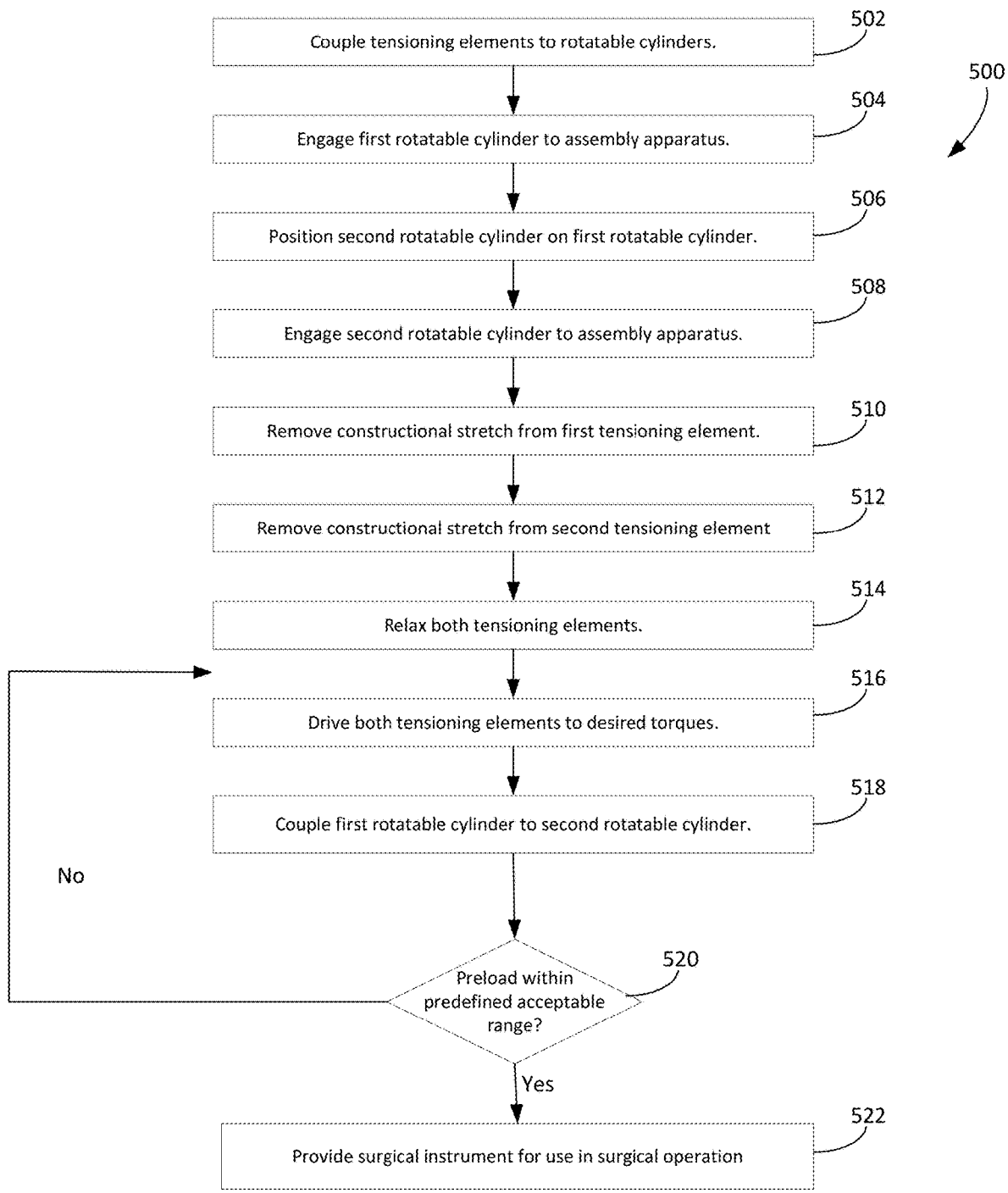
FIG. 13 is a flow chart illustrating a method of tensioning a cable of a drive assembly for a surgical instrument.

The surgical instruments described herein are assembled and manufactured through one or more processes described herein, enabling them to be mountable to manipulator for performing surgical procedures. FIG. 13 illustrates the assembly process 500 for providing preload to a tensioning element, e.g., a cable, of a drive assembly for a surgical instrument. In particular, the assembly process 500 is implemented to provide preloads to multiple tensioning elements coupled to a single input device. The assembly process 500 will be described in the context of the assembly apparatus 400 and the input device 300, the individual components of which are described above.

At step 502 of the assembly process 500, the tensioning elements 302a, 302b are coupled to the first and second drive shafts 304, 306. Referring back to FIG. 10, the tensioning elements 302a, 302b are also coupled to the distal end component 428, e.g., the end effector, the wrist joint, etc., of the surgical instrument. In some implementations, proximal ends of the tensioning elements 302a, 302b are wrapped around the first and second drive shafts 304, 306, respectively. The proximal ends of the tensioning elements 302a, 302b are, for example, attached to the first drive shaft 304 and the second drive shaft 306 by purely frictional couplings, absent additional connection hardware (e.g., crimps or other fasteners). The proximal ends of the tensioning elements 302a, 302b can be wound around the first drive shaft 304 and the second drive shaft 306. In some examples, coupling proximal ends end of the tensioning elements 302a, 302b to the first drive shaft 304 and the second drive shaft 306 includes routing the tensioning elements 302a, 302b through two or more sharp bends of a tortuous path, winding the tensioning elements 302a, 302b around a spool, and then routing the tensioning elements 302a, 302b along an outwardly facing helical groove.

Distal ends of the tensioning elements 302a, 302b are coupled to the distal end component 428. In some examples, the distal ends of the tensioning elements 302a, 302b are attached to the distal end component 428 through connection hardware, such as crimps or fasteners.

Alternatively or additionally, the tensioning elements 302a, 302b form a continuous cable that is routed through the distal end component 428. The distal end component 428 is fixed relative to the instrument shaft, and the continuous cable is routed through the instrument shaft, through the distal end component 428, and back through the instrument shaft such that the two ends of the continuous cable can be coupled to the first drive shaft 304 and the second drive shaft 306.

In some implementations, step 502 is a manual operation in which a human operator manually couples the tensioning elements 302a, 302b to the first and second drive shafts 304, 306. The human operator manually routes the tensioning elements 302a, 302b through the instrument shaft and manually couples the tensioning elements 302a, 302b to both the distal end component 428 and the first and second drive shafts 304, 306.

At step 504, the first drive shaft 304 is engaged to the assembly apparatus 400 so that the assembly apparatus 400 is operable to drive the first drive shaft 304. In particular, the first drive mechanism 402 of the assembly apparatus 400 is engaged to the first drive shaft 304. In some examples, the first drive shaft 304 is installed in a housing of a drive assembly of the surgical instrument. The drive assembly is mounted onto the first drive mechanism 402 to engage the first drive shaft 304 to the assembly apparatus 400.

In some implementations, a human operator manually mounts the drive assembly onto the first drive mechanism 402 of the assembly apparatus 400. When the human operator mounts the drive assembly onto the first drive mechanism 402, the first drive shaft 304 is axially aligned with the arm 405 of the assembly apparatus 400 to facilitate engagement of the second drive mechanism 404 with the second drive shaft 306 at step 508 described herein.

At step 506, the second drive shaft 306 is positioned on the first drive shaft 304. The second drive shaft 306 is positioned relative to the first drive shaft 304 such that the first and second drive shafts 304, 306 are disengaged from one another, e.g., are in the disengaged state. If the first and second drive shafts 304, 306 include an engagement mechanism similar to the engagement mechanism described with respect to the input device 126, the second drive shaft 306 is positioned on the first drive shaft 304 with splines of the first drive shaft 304 disengaged from splines of the second drive shaft 306. Specifically, the first and second drive shafts 304, 306 are positioned relative to one another such that the splines of the first drive shaft 304 and the second drive shaft 306 are not in a meshed engagement that inhibits relative rotation of the first drive shaft 304 and the second drive shaft 306. Furthermore, if the first drive shaft 304 includes snap fingers, the snap fingers are not engaged to a ridge on the second drive shaft 306 such that the first and the second drive shafts 304, 306 are axially movable relative to one another. In some examples, the human operator manually positions the second drive shaft 306 on the first drive shaft 304.

Because the first and second drive shafts 304, 306 are in the disengaged state, the first and second drive shafts 304, 306 are independently rotatable. In this regard, the first and second tensions can be independently applied to the tensioning elements 302a, 302b. Independent rotation of the first and second drive shafts 304, 306 can be performed when the second drive shaft 306 is placed over the first drive shaft 304, rotationally supported by the support stem of the second drive shaft 306 and in the disengaged state, e.g., with splines of the drive shafts 304, 306 disengaged and/or the friction fit between the drive shafts 304, 306 disengaged. Independent rotation of the first drive shaft 304 and the second draft shaft 306 may be performed by separately powering the first and second drive mechanisms 402, 404 via the first and second motors 406, 408. In some examples, the first and second drive shafts 304, 306 can be rotated alternatively, with one of the components being held fixed while the other is driven. In some other examples, the first and second drive shafts 304, 306 can be rotated simultaneously.

At step 508, the second drive mechanism 404 is engaged to the second drive shaft 306. Specifically, as described herein, the arm 405 axially engages the second drive mechanism 404 with the second drive shaft 306 and then rotationally engages the second drive mechanism 404. The assembly apparatus 400 can perform an automated process to facilitate engagement of the second drive mechanism 404 and the second drive shaft 306. In this regard, during step 508, the assembly apparatus 400 operates the third motor 410 to move the arm 405 axially, thereby engaging the second drive mechanism 404 with the second drive shaft 306 in the axial direction.

In some implementations, the bosses 409 of the second drive mechanism 404 are engaged to the ramped recesses 316 of the second drive shaft 306. To detect engagement of the second drive mechanism 404 to the ramped recesses 316, in some examples, the third motor 410 is rotate a predetermined amount to move the arm 405 a predetermined distance that will result in the bosses 409 being axially engaged in the ramped recesses 316. In this regard, the third motor 410 is controlled based on signals that are indicative of the position of the third motor 410 and that are generated by the encoder 416 associated with the third motor 410.

The assembly apparatus 400 then operates the second motor 408 to rotate the arm 405 about the longitudinal axis until the bosses 409 are engaged to the stops 324, thereby rotationally engaging the second drive mechanism 404 with the second drive shaft 306. To detect engagement of the bosses 409 to the stops 324, the second motor 408 is rotated a predetermined amount to move the arm 405 a predetermined distance that will result in the bosses 409 being engaged to the stops 324. In this regard, the second motor 408 is controlled based on signals that are indicative of the position of the second motor 408 and that are generated by the encoder 414 associated with the second motor 408. With both the first drive mechanism 402 engaged with the first drive shaft 304 and the second drive mechanism 404 engaged with the second drive shaft 306, the first motor 406 and the second motor 408 can be operated to rotate the first and second drive shafts 304, 306 to apply tensile loads to the tensioning elements 302a, 302b.

In some implementations, after the arm 405 is engaged to the second drive shaft 306, the arm 405 is moved longitudinally away from the first drive shaft 304. The second drive shaft 306 is translated away from the first drive shaft 304 so that the drive shafts 304, 306 are not contacting one another. This can reduce friction between the drive shafts 304, 306 when they are rotated relative to one another.

At step 510 and 512, constructional stretches from the first and second tensioning elements 302a, 302b are removed. In some implementations The first and second tensioning elements 302a, 302b are multi-filament cables that each has a constructional stretch that can contribute to non-linear relationships between the tensions in the tensioning elements 302a, 302b and the torques applied to the drive shafts 304, 306. The cables include a core and multiple filaments wrapped around the core. When the cables are initially fabricated, there may exists spaces between the core and the filaments and spaces between the individual filaments. Tensile loads applied to the first and second tensioning elements 302a, 302b may result in the core and the filaments moving toward one another, thereby reducing the size of the spaces. The movement of the core and the filaments may result in an initial constructional stretch, thereby causing an initial elongation of the first and second tensioning elements 302a, 302b. The removal of constructional stretch in steps 510 and 512 can enable the elongation of the first and second tensioning elements 302a, 302b to be more predictable during the surgical procedure. As a result, during the surgical procedure, a given torque applied to drive the input device 300 can produce more predictable motion of the end effector of the surgical instrument. In some examples, with the constructional stretch removed, the relationship between the given torque and the motion of the end effector is linear.

In some implementations, the constructional stretch is removed from each of the first and second tensioning elements 302a, 302b by, for example, cyclically applying tension to each of the first and second tensioning elements 302a, 302b. During a cycle of applied tension, a tension force is applied to the tensioning element and then released. The cyclic application of tensions can enable removal of constructional stretch at lower overall loads.

To apply the tension force, the first motor 406 and the second motor 408 are operated to rotate first and second drive shafts 304, 306 in a direction that causes the tensioning elements 302a, 302b to wrap around the first and second drive shafts 304, 306, e.g., such that the bosses 409 move toward the stops 324. To release the tension force, the first motor 406 and the second motor 408 are operated to rotate the first and second drive shafts 304, 306 such that the bosses 409 move away from the stops 324. As the tension force is released, the stops 324 move with the bosses 409, thereby keeping the arm 405 rotationally engaged with the stops 324 and the second drive mechanism 404. In some examples, the number of cycles of tension is between, for example, 3 and 20, e.g., 3 to 10, 5 to 15, 10 to 20, etc. The tension forces applied to remove the constructional stretches is, for example, 100% to 200% of the maximum allowed tension in.

In some implementations, steps 510 and 512 are performed simultaneously. If the constructional stretch is removed from both the first tensioning element 302a and the second tensioning element 302b at the same time, the first and second tensioning elements 302a, 302b may experience a greater amount of tension. In some implementations, to reduce the amount of tension experienced by each of the first and second tensioning elements 302a, 302b during the removal of the constructional stretches, steps 510 and 512 are performed sequentially, with the constructional stretch of the first tensioning element 302a being removed before the constructional stretch of the second tensioning element 302b being removed.

At step 514, the first and second tensioning elements 302a, 302b are relaxed, e.g., the tension forces applied to the first and second tensioning elements 302a, 302b are removed. The first and second tensioning elements 302a, 302b are relaxed after the constructional stretches are removed. In some examples, the first and second tensioning elements 302a, 302b are relaxed until the static torques experienced by the first and second motors 406, 408 are at predetermined levels. The motors 406, 408 are repositioned to relax the first and second tensioning elements 302a, 302b, for example, by rotating in a manner to feed out the first and second tensioning elements 302a, 302b. The motors 406, 408 are moved to a position in which static torques on the motors 406, 408, e.g., due to static tensions on the first and second tensioning elements 302a, 302b, are below the predetermined levels.

In some examples, the predetermined levels for the torques is 0. In some examples, the predetermined levels are greater than 0. The predetermined levels are sufficiently high to ensure that the first and second tensioning elements 302a, 302b remain coupled to the distal end component, in particular, so that the tensioning elements 302a, 302b are not slack. By starting the process to apply the preloads to the tensioning elements 302a, 302b while the torques are at known and at relatively low levels, the preloads applied during step 516 can be more accurately tuned to desired values.

At step 516, a first tension is applied to the tensioning element 302a, and a second tension is applied to the tensioning element 302b. In some examples, the first and second tensions correspond to the desired preloads for the tensioning elements 302a, 302b. To apply the tensions, the first motor 406 and the second motor 408 are driven to rotate the first and second drive shafts 304, 306, thereby rotating the first and second rotatable cylinders 318, 320. In particular, the first motor 406 and the second motor 408 are operated to apply torques to the first and second drive shafts 304, 306.

In some implementations, the first and second tensions correspond to target tensions selected by the human operator. The human operator provides an input to the assembly apparatus 400 indicative of the target tensions. The target tensions, in some cases, correspond to target preloads on the tensioning elements 302a, 302b. As described herein, in some examples, the target tensions account for external loads that are overcome to apply the preloads on the tensioning elements 302a, 302b.

In some implementations, as shown in FIG. 11, the distal end component 428 is positioned within a nest 430 at step 516. The nest 430 inhibits motion of the distal end component 428 such that tensions can be applied to the tensioning elements 302a, 302b without causing motion of the first drive shaft 304 and the second drive shaft 306. The nest 430 can maintain the distal end component 428 at a central position within a range of motion of the degree of freedom enabled by the first and second tensioning elements 302a, 302b. In this regard, the first and second tensions applied to the tensioning elements 302a, 302b are equal to one another. The assembly apparatus 400 controls the motors 406, 408 to apply equal predetermined levels of torque while the position of the distal end component 428 is maintained. In this regard, when the distal end component 428 is removed from the nest 430, the distal end component 428 remains at the central position within the range of motion. The central position corresponds to the neutral position absent any drive torque applied to the first drive shaft 304. This neutral position can correspond to the position of the distal end component 428 when the surgical instrument is provided for use in a surgical procedure before the input device 300 is torqued during the surgical procedure.

In some cases, the distal end component 428 is positioned within the nest 430 after the assembly apparatus 400 is engaged to both the first drive shaft 304 and the second drive shaft 306. In this regard, the constructional stretches can be removed at steps 510, 512 with the distal end component 428 positioned within the nest 430.

While the first and second tensions applied in step 516 are described as corresponding to the preloads, in some implementations, the first and second tensions correspond to the preloads added to external loads along the entire drivetrain to move the end effector of the surgical instrument. Rather than corresponding to target preloads, the target tensions correspond to the sum of target preloads and additional tensions to overcome the external loads. Portions of the first and second tensions, for example, overcome frictional loads along the drivetrain. The frictional loads include, for example, frictional loads on the first and second tensioning elements 302a, 302b, frictional loads on the first drive mechanism 402, frictional loads at the joint about which the distal end component 428 rotates, etc. The frictional loads include static frictional loads and/or dynamic frictional loads. The remainder of the first and second tensions corresponds to the preloads on the tensioning elements 302a, 302b. Based on this friction compensation, the target tensions on the tensioning elements 302a, 302b can be selected to achieve target preloads.

In some examples, desired preloads for the tensioning elements 302a, 302b can be computed based on estimated static frictional forces on the tensioning elements 302a, 302b. The frictional forces are estimated based on minimum required torques applied by the motors 406, 408 to initiate relative rotation of the first drive shaft 304 and the second drive shaft 306. The minimum required torques correspond to the amount of torque needed to cause motion of the tensioning elements 302a, 302b. In some implementations, low currents are applied to the motors 406, 408 such that the torques applied to the drive shafts 304, 306 are relatively low. The applied currents are increased until motion of the drive shafts 304, 306 are detected. The torques at the beginning of motion of the drive shafts 304, 306 are indicative of the frictional forces on the tensioning elements 302a, 302b. In this regard, the first and second tensions applied to the tensioning elements 302a, 302b in step 516 account for the estimated frictional forces.

In some examples, the static frictional force on the tensioning element 302a is estimated independently from the static frictional force on the tensioning element 302b. To estimate the frictional force on the tensioning element 302a, the first motor 406 drives the first drive shaft 304 while the second motor 408 is fixed. The torque sensor 418 coupled to the first motor 406 generates a signal indicative of the minimum required torque to drive the first drive shaft 304, and the value for this minimum required torque is indicative of the frictional force on the tensioning element 302a. To estimate the frictional force on the tensioning elements 302b, the second motor 408 drives the second drive shaft 306 while the first motor 410 is fixed. The torque sensor 420 coupled to the second motor 408 generates a signal indicative of the minimum required torque to drive the second drive shaft 306, and the value for this minimum required torque is indicative of the frictional force on the tensioning element 302b.

In some implementations, dynamic frictional loads on the tensioning elements 302a, 302b are estimated. The tensioning elements 302a, 302b are coupled to an external torque sensor, e.g., independent of the torque sensors 418, 420 coupled to the motors 406, 408. The first motor 406 and the second motor 408 each apply gradually increasing tensile loads on the first and second tensioning elements 302a, 302b. The tensile loads are then gradually decreased. Differences between the torque indicated by signals generated by the external torque sensor and the torques indicated by the torque sensors 418, 420 are computed. These differences are indicative of the dynamic frictional loads at different values of tensile force on the tensioning elements 302a, 302b, e.g., through the range of tensile load values applied to the tensioning elements 302a, 302b.

At step 518, the first drive shaft 304 and the second drive shaft 306 are engaged to one another while the first and second tensions are maintained. In some examples, the first drive shaft 304 and the second drive shaft 306 are separated from one another such that they are not contacting one another. The longitudinal translation, for example, causes the second drive shaft 306 to contact the first drive shaft 304, and then causes the second drive shaft 306 to engage the first drive shaft 306 in a manner that couples motion of the drive shafts 304, 306. The first drive shaft 304 and the second drive shaft 306 can be placed in the engaged state such that the first drive shaft 304 and the second drive shaft 306 can be rotationally coupled to one another. In some examples, if the input device 300 includes the engagement mechanism of the input device 126 or the input device 200, the second drive shaft 306 is translated toward the first drive shaft 304 into the engaged state.

In some implementations, in accordance to the engagement mechanism described with respect to the input device 126, the splines of the first drive shaft 304 and the splines of the second drive shaft 306 form a meshed engagement to inhibit relative rotation and translation between the first and second drive shafts 304, 306. Step 518 includes securing the second draft shaft 306 to the first drive shaft 304 by engaging the splines of the second drive shaft 306 with an outer surface of the first drive shaft 304, such that relative rotation between the first drive shaft 304 and the second drive shaft 306 is inhibited by the engaged splines. In some examples, engaging the splines of the second drive shaft 306 includes meshing the splines with a mating set of vertical splines of the first drive shaft 304.

In some implementations, securing the second drive shaft 306 to the first drive shaft 304 further includes engaging snap fingers of the first drive shaft 304 with an undercut ridge formed along an internal bore of the second drive shaft 306, such that relative vertical movement between the first drive shaft 304 and the second drive shaft 306 is resisted.

The second drive shaft 306 can be secured to the first drive shaft 304 to place the components in an engaged state by simply pressing the second drive shaft 306 down over the first drive shaft 304 to simultaneously engage the splines and the snap fingers. A downward force may be applied to the second drive shaft 306 to engage the first drive shaft 304 and the second drive shaft 306.

Alternatively, in accordance to the engagement mechanism described with respect to the input device 200, the tapered geometry of a bore of the second drive shaft 306 frictionally engages with the tapered geometry of a support stem of the first drive shaft 304. Securing the second drive shaft 306 may include applying a downward vertical force against the second drive shaft 306 to drive it down against the stem portion of the first drive shaft 304. The downward vertical force causes the radially tapered surface of the lower bore portion of the second drive shaft 306 to bear against the radially tapered outer surface of the support stem of the first drive shaft 304. The mutual force exerted by these mating surfaces against one another provides sufficient friction to inhibit relative movement between the first drive shaft 304 and second drive shaft 306. In some examples, the radial taper of the surfaces defines a self-locking taper, allowing the second drive shaft 306 and drive shaft to remain engaged absent the downward force.

In some examples, in step 518, the first drive shaft 304 and the second drive shaft 306 can be engaged in an automated process facilitated by the assembly apparatus 400. In some implementations, the third motor 410 drives the arm 405 axially toward the first drive shaft 304 such that the second drive shaft 306 is translated toward the first drive shaft 304. The longitudinal translation of the second drive shaft 306 causes the second drive shaft 306 to engage the first drive shaft 304.

In some examples, rather than being coupled to one another in an automated process, the first drive shaft 304 and the second drive shaft 306 are engaged in a manual operation in which the human operator manually engages the second drive shaft 306 with the first drive shaft 304. The first drive shaft 304 and the second drive shaft 306 are manually locked together. The human operator, for example, pushes the second drive shaft 306 against the first drive shaft 304 to place the first and second drive shafts 304, 306 in the engaged state. In some other examples, a set screw may be inserted through coaxially aligned bores of the second drive shaft 306 and support stem to maintain the downward force that facilitates the taper friction fit coupling.

In some examples in which the first drive shaft 304 and the second drive shaft 306 are manually locked together, operator feedback is provided. The operator feedback, for example, indicates if an operator error has occurred. The operator feedback can alert the operator to actions that can cause, for example, unequal preloads to be applied to the first and second tensioning elements 302a, 302b, excessive slack in the tensioning elements 302a, 302b, excessive preload in the tensioning elements 302a, 302b, etc. An operator error can occur if the human operator rotates the first drive shaft 304 relative to the second drive shaft 306 by an amount greater than a predetermined threshold.

In some examples, the encoder 412 and/or the encoder 414 generates a signal indicative of a relative rotation between the first drive shaft 304 and the second drive shaft 306. Specifically, the signal from the encoder 412 can indicate that the first drive shaft 304 is rotating during the manual locking operation, and the signal from the encoder 414 can indicate that the second drive shaft 306 is rotating during the manual locking operation. If relative motion between the first drive shaft 304 and the second drive shaft 306 exceeds a predetermined threshold, an alarm is issued to indicate to the operator that the operator is performing an action that may result in an operator error. In some implementations, the signals from the encoders 412, 414 are indicative of a loop length of the first tensioning element 302a and the second tensioning element 302b. The loop length can be indicative of the preloads on the tensioning elements 302a, 302b, e.g., applied during step 516. The loop length corresponds to the sum of (i) a first length measured from where the first tensioning element 302a is attached to the first drive shaft 304 to where the first tensioning element 302a is coupled to the distal end component 428 and (ii) a second length measured from where the second tensioning element 302b is attached to the second drive shaft 306 to where the second tensioning element 302b is attached to the distal end component 428. The signals of the encoders 412, 414 are indicative of changes in the loop length. Operator feedback is provided to maintain the loop length. In particular, the operator feedback can indicate to the human operator that the manual locking operation should be adjusted to avoid changing the loop length.

In some examples, the torque sensor 418 and/or the torque sensor 420 generates a signal indicative of a torque applied to the first drive shaft 304 and/or the second drive shaft 306. The torque sensor 418 can indicate that a torque is being applied to the first drive shaft 304, and the torque sensor 420 can indicate that a torque is being applied to the second drive shaft 306. If the signal indicates a torque level greater than a predetermined threshold, an alarm is issued to indicate to the operator that the operator is performing an action that may result in an operator error.

After the first drive shaft 304 and the second drive shaft 306 are placed in the engaged state, the first and second tensioning elements 302a, 302b are coupled to one another. The resultant preload of the first and second tensioning elements 302a, 302b can be measured for verification that the resultant preload correspond to the target preload. At step 520, the resultant preload on the coupled first and second tensioning elements 302a, 302b is estimated.

In some implementations, in preparation for estimating the resultant preload, the arm 405 is disengaged from the input device 300. The arm 405 is rotated to disengage the bosses 409 from the stops 324, and then the arm 405 driven longitudinally away from the input device 300 to disengage the bosses 409 from the ramped recesses 316.

During step 520, the input device 300 is driven in a first direction that increases the tension on the first tensioning element 302a while decreasing the tension on the second tensioning element 302b. In some examples, the first motor 406 is operated such that the torque measured by the torque sensor 418 is greater than twice the target preload on the first tensioning element 302a. The second tensioning element 302b may go slack during such an operation of the first motor 406. An amount of rotation of the first motor 406 is determined based on signals from the encoder 412.

During step 520, the input device 300 is driven in an opposite second direction that increases the tension on the second tensioning element 302b while decreasing the tension on the first tensioning element 302a. The first motor 406 is operated such that the torque measured by the torque sensor 418 is greater than twice the target preload on the second tensioning element 302b. The first tensioning element 302a may go slack during such an operation of the first motor 406. An amount of rotation of the first motor 406 is determined based on signals from the encoder 412.

A sum of the amount of rotation of the first motor 406 in the first direction and the amount of rotation of the first motor 406 in the second direction is an estimate of the preload tension. The sum of the amounts of rotation are indicative of the resultant preload of the coupled first tensioning element 302a and second tensioning element 302b. If the resultant preload is either too high or too low, e.g., if the resultant preload is outside of a predefined acceptable range, this may potentially cause motion for the end effector that cannot be easily predicted using feedback control. The predefined acceptable range can be defined based on a type of the surgical instrument.

To improve predictability of the motion of the end effector during a surgical procedure, if the sum of the motions of the first motor 406 during step 520 is outside of the predefined acceptable range as specified for the particular surgical instrument type, the first drive shaft 304 and the second drive shaft 306 can be disengaged from one another. In some examples, the operator can manually disengage the first drive shaft 304 from the second drive shaft 306 as described herein. In other examples, the second motor 408 and the third motor 410 are operated to reengage the arm 405 with the second drive shaft 306. The arm 405 is then driven longitudinally to disengage the second drive shaft 306 from the first drive shaft 304, thereby rotationally decoupling these components from one another. As noted above, the snap fingers or the tapered stem support stem of the first drive shaft 304 may be designed to permit the release of the second drive shaft 306 from engagement with the first drive shaft 304 when the second drive shaft 306 driven axially away from the first drive shaft 304. For example, tapered geometry of the first drive shaft 304 and tapered geometry of the second drive shaft 306 can be disengaged from one another when a sufficient amount of axial force is applied to the second drive shaft 306. As such, further tensioning can be performed by releasing the second drive shaft 306, again independently rotating the second drive shaft 306 and the first drive shaft 304 in accordance to the process described with respect to step 516, and then re-engaging the first drive shaft 304 and the second drive shaft 306 in accordance to the process described with respect to step 518. The preload can then be verified again at step 520.

The remaining steps to assemble the surgical instrument, if the preload is within the predefined acceptable range, are then completed. In some examples, preloads are applied to other tensioning elements of the surgical instrument attached to other drive inputs of the surgical instrument. At step 522, the surgical instrument in its assembled form is provided for use in a surgical procedure. The surgical instrument is, for example, provided to an operator. The operator sterilizes the surgical instrument prior to use in the surgical procedure. The surgical instrument is then mounted to the patient side assembly, and the patient side assembly is remotely controlled to manipulate the surgical instrument during the surgical procedure.

Example Computer Systems

Figure 14:
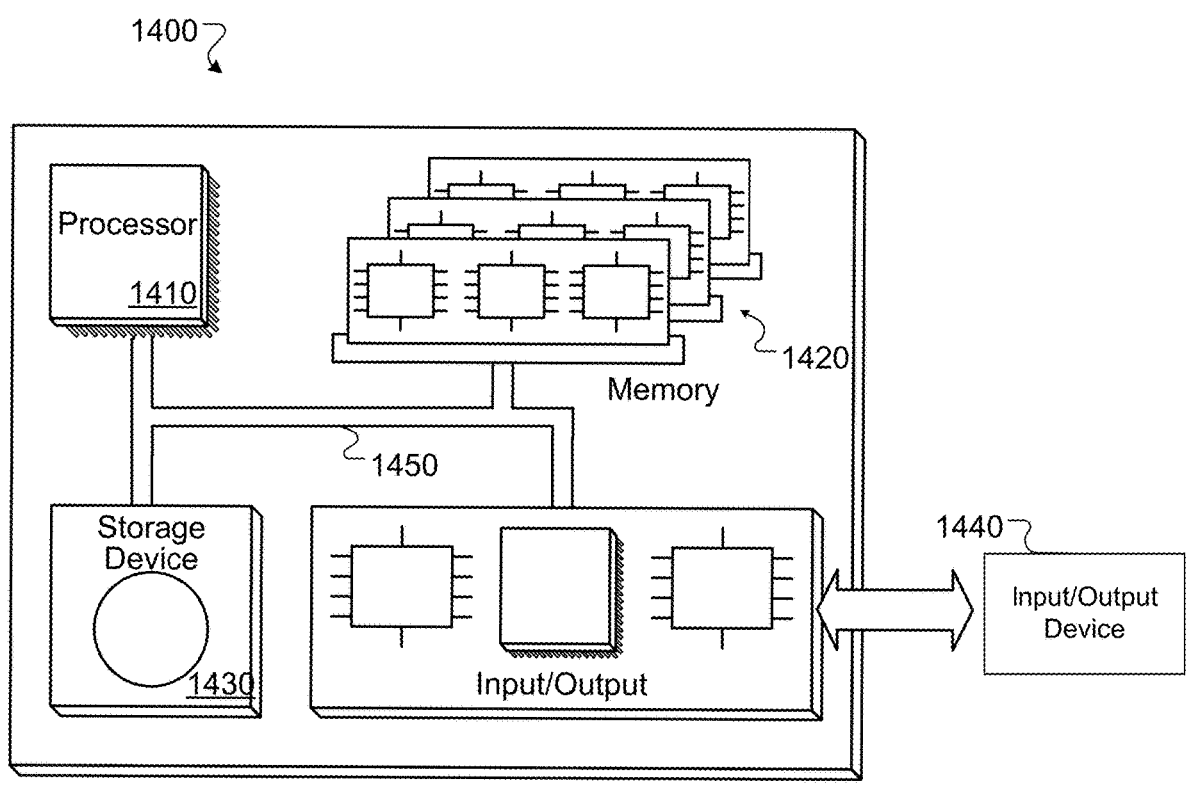
FIG. 14 is a schematic diagram of an example of a computer system.

Controllers and any associated components described herein can be part of a computing system that facilitates control of the insertion systems according to processes and methods described herein. FIG. 14 is a schematic diagram of an example of a computer system 1400 that can be used to implement a controller, e.g., the controller of the assembly apparatus 400, a controller of the manipulator 112, etc., described in association with any of the computer-implemented methods described herein. The system 1400 includes components such as a processor 1410, a memory 1420, a storage device 1430, and an input/output device 1440. Each of the components 1410, 1420, 1430, and 1440 are interconnected using a system bus 1450. The processor 1410 is capable of processing instructions for execution within the system 1400. In some examples, the processor 1410 is a single-threaded processor, while in some cases, the processor 1410 is a multi-threaded processor. The processor 1410 is capable of processing instructions stored in the memory 1420 or on the storage device 1430 to display graphical information for a user interface on the input/output device 1440.

Memory storage for the system 1400 can include the memory 1420 as well as the storage device 1430. The memory 1420 stores information within the system 1400. The information can be used by the processor 1410 in performing processes and methods described herein. In some examples, the memory 1420 is a computer-readable storage medium. The memory 1420 can include volatile memory and/or non-volatile memory. The storage device 1430 is capable of providing mass storage for the system 1400. In general, the storage device 1430 can include any non-transitory tangible media configured to store computer readable instructions. Optionally, the storage device 1430 is a computer-readable medium. Alternatively, the storage device 1430 may be a floppy disk device, a hard disk device, an optical disk device, or a tape device.

The system 1400 includes the input/output device 1440. The input/output device 1440 provides input/output operations for the system 1400. In some examples, the input/output device 1440 includes a keyboard and/or pointing device. In some cases, the input/output device 1440 includes a display unit for displaying graphical user interfaces.

The features of the methods and systems described in this application can be implemented in digital electronic circuitry, or in computer hardware, firmware, or in combinations of them. The features can be implemented in a computer program product tangibly stored in an information carrier. The information carrier can be, for example, a machine-readable storage device, for execution by a programmable processor. Operations can be performed by a programmable processor executing a program of instructions to perform the functions described herein by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages. The computer program can be deployed in any form, including as a stand-alone program or as a module, component, subroutine, or other unit suitable for use in a computing environment.

Generally, a computer will also include, or be operatively coupled to communicate with, one or more mass storage devices for storing data files. Such devices can include magnetic disks, such as internal hard disks and removable disks, magneto-optical disks, and optical disks. Storage devices suitable for storing the computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

The processor 1410 carries out instructions related to a computer program. The processor 1410 can include hardware such as logic gates, adders, multipliers and counters. The processor 1410 can further include a separate arithmetic logic unit (ALU) that performs arithmetic and logical operations.

The use of terminology such as "top," "bottom," "over," "upward," "downward," "upper," "lower," etc. throughout the specification and claims is for describing the relative positions of various components of the system and other elements described herein. Similarly, the use of any horizontal or vertical terms to describe elements is for describing relative orientations of the various components of the system and other elements described herein. Unless otherwise stated explicitly, the use of such terminology does not imply a particular position or orientation of the system or any other components relative to the direction of the Earth gravitational force, or the Earth ground surface, or other particular position or orientation that the system other elements may be placed in during operation, manufacturing, and transportation.

A number of implementations of the invention have been described. Nevertheless, it will be understood that various modifications may be made without departing from the spirit and scope of the inventions. In addition, it should be understood that various described components and features optionally may be combined, so that one or more features of one implementation may be combined with, or substituted for, one or more features of another implementation consistent with the inventive aspects.

What is claimed is:

1. A method of manufacturing a surgical instrument mountable to a remotely controllable manipulator configured to operate the surgical instrument, the method comprising:
applying a first tension to a first tensioning element coupled to a first rotatable cylinder of the surgical instrument by using a first motor to apply a first torque to the first rotatable cylinder;
applying a second tension to a second tensioning element coupled to a second rotatable cylinder of the surgical instrument by using a second motor to apply a second torque to the second rotatable cylinder; and
maintaining the first and second tensions in the first and second tensioning elements while the first rotatable cylinder is being locked to the second rotatable cylinder;
wherein the first tensioning element and the second tensioning element are each coupled to a distal end component of the surgical instrument and are coupled to one another such that a tension in one of the first tensioning element and the second tensioning element is transmitted at least in part to the other of the first tensioning element and the second tensioning element.

2. The method of claim 1, wherein applying the first tension and the second tension comprises applying the first tension and the second tension based on an operator input indicative of target tensions.

3. The method of claim 1, further comprising removing a first constructional stretch from the first tensioning element and a second constructional stretch from the second tensioning element before applying the first and second tensions to the first and second tensioning elements.

4. The method of claim 3, further comprising relaxing the first and second tensioning elements after removing the first constructional stretch and the second constructional stretch and before applying the first and second tensions to the first and second tensioning elements.

5. The method of claim 3, wherein removing the first constructional stretch and the second constructional stretch comprises cyclically applying a tension to each of the first and second tensioning elements.

6. The method of claim 1, wherein the first rotatable cylinder is manually lockable to the second rotatable cylinder, and the method further comprises providing an operator feedback while an operator is manually locking the first and second rotatable cylinders together.

7. The method of claim 6, further comprising:
measuring positions of the first and second rotatable cylinders to monitor a loop length; and
providing the operator feedback to maintain the loop length.

8. The method of claim 7, wherein measuring the positions of the first and second rotatable cylinders comprises measuring positions of the first and second motors based on a plurality of signals from a plurality of encoders coupled to the first and second motors.

9. The method of claim 1, further comprising locking the first and second rotatable cylinders by translating the second rotatable cylinder toward the first rotatable cylinder.

10. The method of claim 1, wherein:
applying the first tension to the first tensioning element comprises applying the first tension to the first tensioning element based on a friction force on the first tensioning element, and
applying the second tension to the second tensioning element comprises applying the second tension to the second tensioning element based on a friction force on the second tensioning element.

11. The method of claim 1, wherein the first tension and the second tension are applied while a position of an instrument joint coupled to the first and second tensioning elements is maintained.

12. The method of claim 1, further comprising:
applying a third tension to the first tensioning element while the first and second rotatable cylinders are engaged such that a tension in the second tensioning element is substantially zero,
applying a fourth tension to the second tensioning element while the first and second rotatable cylinders are engaged such that a tension in the first tensioning element is substantially zero, and then
estimating a difference between an amount of rotation when the third tension is applied and an amount of rotation when the fourth tension is applied,
wherein the first tension and the second tension are applied to the first tensioning element and the second tensioning element, respectively, when the difference exceeded a predefined threshold.

13. The method of claim 1, wherein the first tension and the second tension are applied while the first rotatable cylinder and the second rotatable cylinder are disengaged from one another, and the method further comprises engaging the first rotatable cylinder to the second rotatable cylinder.

14. A method of manufacturing a surgical instrument mountable to a remotely controllable manipulator configured to operate the surgical instrument, the method comprising:
applying a tension to a first tensioning element coupled to a first rotatable cylinder of the surgical instrument by using a first motor to rotate the first rotatable cylinder relative to a second rotatable cylinder of the surgical instrument; and
maintaining the tension in the first tensioning element and maintaining the tension in a second tensioning element coupled to the second rotatable cylinder while the first rotatable cylinder is being locked to the second rotatable cylinder;
wherein the first tensioning element and the second tensioning element are coupled to a distal end component of the surgical instrument and are configured such that a tension in one of the first tensioning element and the second tensioning element is transmitted at least in part to the other of the first tensioning element and the second tensioning element.

15. The method of claim 14, wherein applying the tension comprises applying the tension based on an operator input indicative of a target tension.

16. The method of claim 14, further comprising removing a first constructional stretch from the first tensioning element and removing a second constructional stretch from the second tensioning element before applying the tension.

17. The method of claim 16, further comprising relaxing the first and second tensioning elements after removing the first constructional stretch and the second constructional stretch and before applying the tension.

18. The method of claim 16, wherein removing the first construction stretch and the second constructional stretch comprises cyclically applying a tension to each of the first and second tensioning elements.

19. The method of claim 14, wherein the first rotatable cylinder is manually lockable to the second rotatable cylinder, and the method further comprises providing an operator feedback while an operator is manually locking the first and second rotatable cylinders together.

20. The method of claim 19, further comprising:
measuring positions of the first and second rotatable cylinders to monitor a loop length; and
providing the operator feedback to maintain the loop length.

21. The method of claim 14, further comprising locking the first and second rotatable cylinders by translating the second rotatable cylinder toward the first rotatable cylinder.

22. The method of claim 14, wherein:
applying the tension to the first tensioning element comprises applying the tension to the first tensioning element based on a friction force on the first tensioning element.

* * * * *